United States Patent
Beisel

(10) Patent No.: US 7,695,466 B2
(45) Date of Patent: Apr. 13, 2010

(54) STYLET FREE FLEXIBLE-TIP EPIDURAL CATHETER AND METHOD OF MAKING

(76) Inventor: Robert F. Beisel, 150 S. Mountain Rd., Robesonia, PA (US) 19551

( * ) Notice: Subject to any disclaimer, the term of this patent is extended or adjusted under 35 U.S.C. 154(b) by 240 days.

(21) Appl. No.: 11/487,594

(22) Filed: Jul. 14, 2006

(65) Prior Publication Data

US 2008/0015547 A1    Jan. 17, 2008

Related U.S. Application Data

(60) Provisional application No. 60/699,252, filed on Jul. 14, 2005.

(51) Int. Cl.
*A61M 25/00* (2006.01)
*A61M 29/00* (2006.01)
*B32B 37/00* (2006.01)

(52) U.S. Cl. .................. 604/525; 264/139; 604/102.02

(58) Field of Classification Search ......... 604/523–525; 264/291
See application file for complete search history.

(56) References Cited

U.S. PATENT DOCUMENTS

| | | | | |
|---|---|---|---|---|
| 3,382,121 A | * | 5/1968 | Sherlock | 156/165 |
| 3,485,234 A | * | 12/1969 | Stevens | 600/434 |
| 3,634,924 A | * | 1/1972 | Blake et al. | 29/447 |
| 3,746,003 A | * | 7/1973 | Blake et al. | 604/102.02 |
| 3,773,034 A | * | 11/1973 | Burns et al. | 600/434 |
| 4,207,364 A | * | 6/1980 | Nyberg | 138/141 |
| 4,385,635 A | * | 5/1983 | Ruiz | 600/435 |
| 4,516,972 A | * | 5/1985 | Samson | 604/526 |
| 4,753,765 A | * | 6/1988 | Pande | 264/149 |
| 4,794,912 A | * | 1/1989 | Lia | 600/152 |
| 5,004,456 A | | 4/1991 | Botterbusch et al. | |
| 5,104,705 A | * | 4/1992 | Quackenbush | 428/36.91 |
| 5,176,660 A | | 1/1993 | Truckai | |
| 5,254,107 A | * | 10/1993 | Soltesz | 604/525 |
| 5,308,342 A | * | 5/1994 | Sepetka et al. | 604/525 |
| 5,314,428 A | * | 5/1994 | Marotta | 604/95.03 |
| 5,385,148 A | * | 1/1995 | Lesh et al. | 600/471 |
| 5,499,981 A | * | 3/1996 | Kordis | 606/41 |
| 5,524,337 A | * | 6/1996 | Houser et al. | 29/825 |
| 5,538,513 A | * | 7/1996 | Okajima | 604/527 |
| 5,582,610 A | * | 12/1996 | Grossi et al. | 606/46 |
| 5,599,326 A | | 2/1997 | Carter | |
| 5,700,253 A | * | 12/1997 | Parker | 604/526 |
| 5,811,043 A | * | 9/1998 | Horrigan et al. | 264/138 |
| 5,899,891 A | | 5/1999 | Racz | |
| 5,899,892 A | * | 5/1999 | Mortier et al. | 604/523 |
| 5,947,939 A | * | 9/1999 | Mortier et al. | 604/523 |

(Continued)

FOREIGN PATENT DOCUMENTS

WO    WO91/07272    5/1991

*Primary Examiner*—Nicholas D Lucchesi
*Assistant Examiner*—Ian K Holloway
(74) *Attorney, Agent, or Firm*—Charles A. Wilkinson; Clinton H. Wilkinson

(57) ABSTRACT

The distal end of a flexible tip epidural catheter is stiffened by the insertion of a stress oriented plastic tubular section into the end of the interior of the catheter removed from a terminal flexible tip and then expanded into contact with the wall of the interior of the catheter interior to stiffen a section approximately the length of an epidural needle in which it is to be used.

7 Claims, 12 Drawing Sheets

U.S. PATENT DOCUMENTS

| | | |
|---|---|---|
| 5,947,940 A | 9/1999 | Beisel |
| 5,961,511 A * | 10/1999 | Mortier et al. ............... 604/527 |
| 5,964,971 A * | 10/1999 | Lunn ........................... 156/86 |
| 5,976,120 A * | 11/1999 | Chow et al. ................. 604/525 |
| 6,059,770 A * | 5/2000 | Peacock et al. ............. 604/526 |
| 6,090,099 A | 7/2000 | Samson et al. |
| 6,152,912 A | 11/2000 | Jansen et al. |
| 6,171,296 B1 | 1/2001 | Chow |
| 6,258,080 B1 | 7/2001 | Samson |
| 6,296,631 B2 | 10/2001 | Chow |
| 6,355,027 B1 | 3/2002 | Le et al. |
| 6,475,209 B1 | 11/2002 | Larson et al. |
| 6,641,563 B1 | 11/2003 | Vitullo et al. |
| 6,673,291 B1 * | 1/2004 | Field et al. ................... 264/139 |
| 7,322,988 B2 * | 1/2008 | Sterud et al. ................. 606/108 |

* cited by examiner

INITIAL MODULUS vs. STRAIN

DISPLACEMENT AT BREAK vs. STRAIN

ULTIMATE BREAK FORCE vs. STRAIN

SHRINKAGE vs. DRAW RATIO

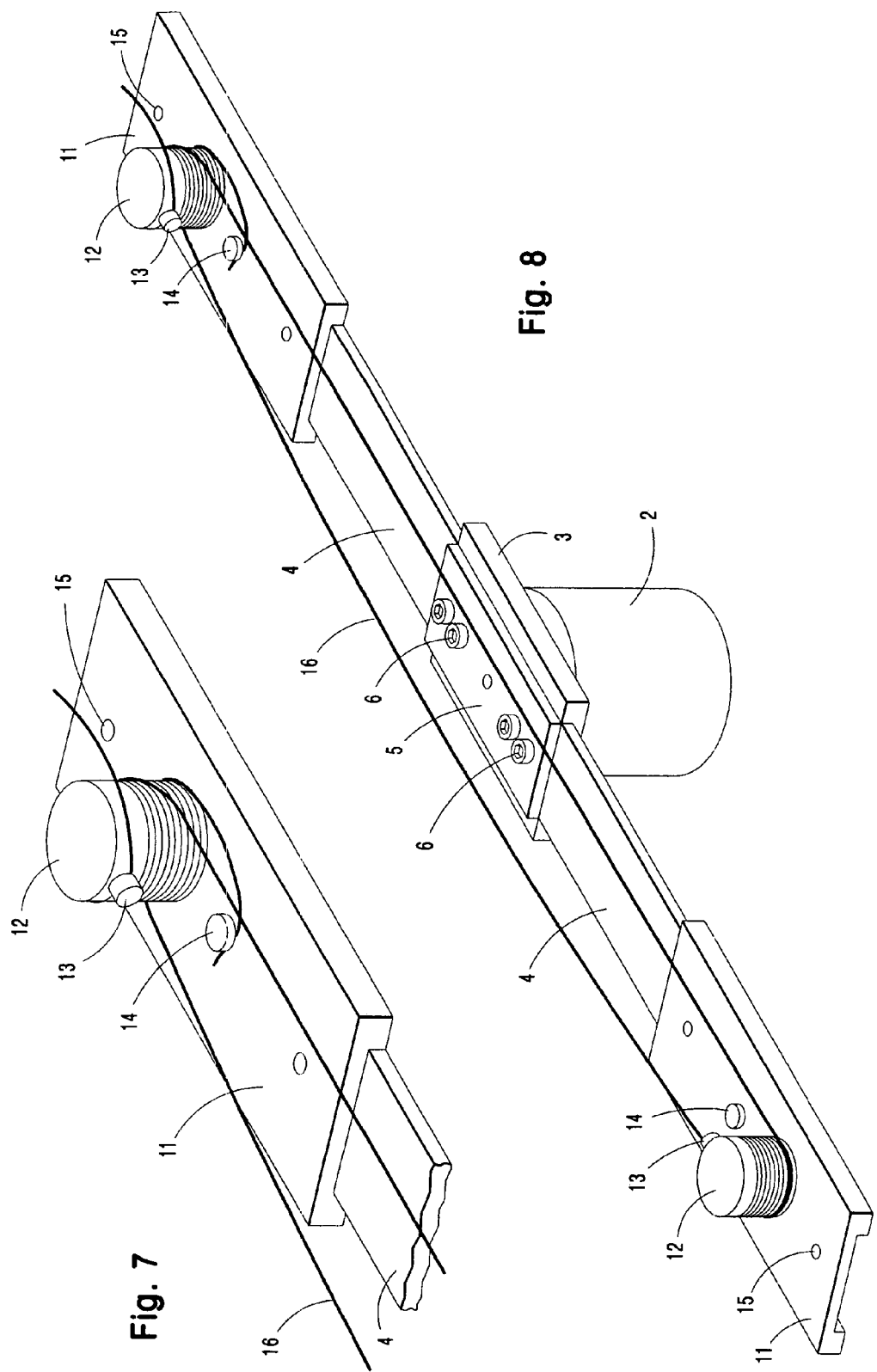

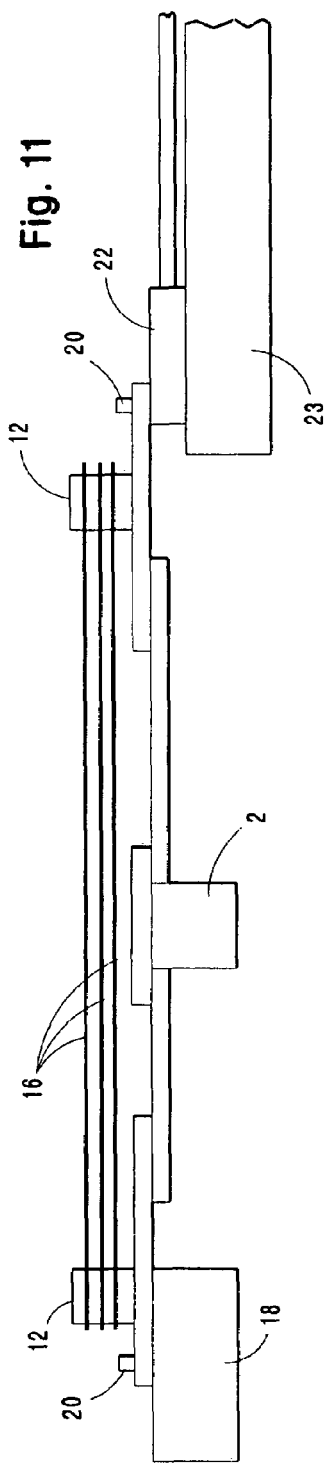
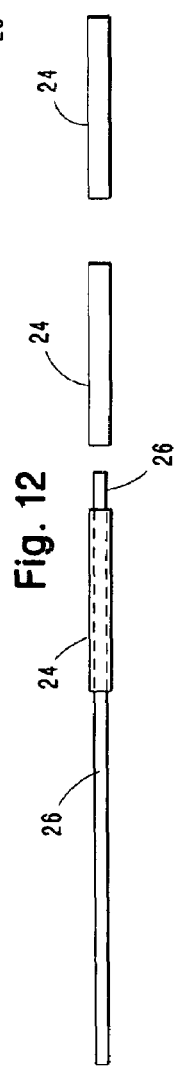
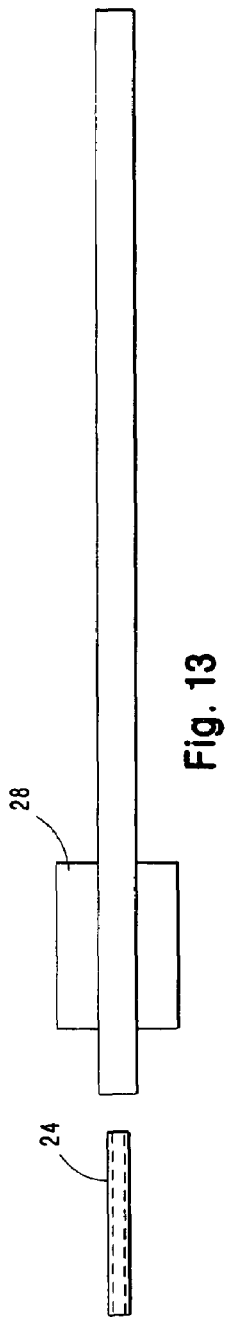
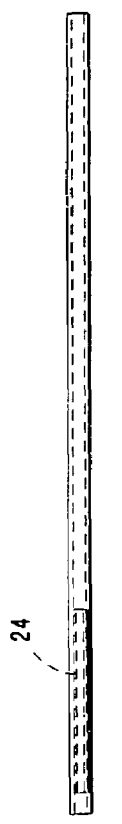

STYLET FREE FLEXIBLE-TIP EPIDURAL CATHETER AND METHOD OF MAKING

RELATED APPLICATIONS

This application claims priority from U.S. Provisional Application 60/699,252 filed Jul. 14, 2005.

BACKGROUND OF THE INVENTION

1. Field of the Invention

This invention relates generally to the administration of local anesthetic and more particularly to so-called epidural catheters for the injection of local anesthetic in the epidural space in the spine.

2. Preliminary Discussion

The name of a popular epidural catheter, Flextip™, itself infers that the distal end is very flexible and more proximal regions of the catheter are less so. Inasmuch as styleted epidural catheters are, for normal uses, professionally unacceptable and have been so for the better part of fifteen years, any viable soft tip epidural must solve the problem of stiffening that section of catheter which must be pushed to advance the catheter past the curved tip of the introducing epidural needle and into the patient's epidural space. It will be apparent to those skilled in the art that this stiffened section must of necessity be located within the epidural needle's length from the distal end of the catheter being inserted. Were this not so, in use when resistance is encountered as the catheter's distal tip transits the tip of the needle and attempts to enter the epidural space, the anesthesiologist would be unable to overcome this resistance by pushing on the extremely flexible and essentially 'unpushable' soft distal tip of the catheter which has not yet entered the needle hub. It will be equally apparent to those skilled in the art that the length of the stiffened section can effectively control the maximum depth to which the catheter can be inserted, in this manner minimizing the likelihood of the catheter's soft tip curling back upon itself and creating a knot that seriously complicates later removal.

3. Discussion of the Prior Art

The first Flextip, disclosed in U.S. Pat. No. 5,004,456 to Botterbusch and Frankhouser, provided for a stiffer proximal section of the catheter with a solid, higher durometer polyurethane tube butt-welded to a 'less than needle's length' section of softer polyurethane tubing.

The Flextip Plus and its later mimics achieve proximal stiffness with a unifilar stainless steel wire coil. The initial tension of the coil provides the catheter with column strength and pushability up to a buckling load, judged initially by some to be less than desirable, especially in fine gage (smaller diameter) catheters. A 'less than needle's length' of highly flexible, stretched coil at the distal end assures a soft, atraumatic tip of a length insufficient to interfere with insertion into the needle.

The catheter described in U.S. Pat. No. 5,947,940 to Beisel offers high strength and low marginal cost, being based on a continuously wound, coated, and processed structure. Despite offering some disclosure about 'providing regional stiffness,' an acceptable method of providing this required regional stiffness has remained illusive.

Vitullo et. al. in U.S. Pat. No. 6,641,563 and U.S. patent application Ser. No. 0040030289 allude to the unsolved problem, that is the need to employ a stylet for inserting such catheters, and deem them less than totally satisfactory.

If one cannot provide the soft tipped catheters with adequate regional stiffness required for insertion into the needle, an attempt to improve thread assist devices, or TADs, seems reasonable. A simple TAD, in the form of a male luer adapter with a small hole that effectively straightens the epidural catheter in its passage through the epidural needle hub, is the very device that allowed first development of stylet free epidurals. Though relatively stiff in comparison to newer flextips, the slightly softer simple tube catheters could be inserted without a stylet using this simple TAD to eliminate the depth of the female luer hub from the column being pushed and, by so shortening the unsupported length, increasing its column strength to a level adequate for insertion.

With the later advent of helical reinforcement in catheters, epidural catheters' distal tips could become much softer, thereby all but eliminating venous cannulation and paresthesiae during their insertion; these simple TADs were, however, unusable with catheters based on U.S. Pat. No. 5,947,940.

Vitullo, et. al. teaches in U.S. Pat. No. 6,641,563 and U.S. patent application Ser. No. 0040030289 the use of an externally applied UV curable or heat-shrinkable sleeve to achieve regional stiffening. Although UV curable materials can be die-coated in continuous deposits, intermittent deposits are very difficult to achieve at best. In addition, UV cured materials lack the optimal tensile properties to enable them to serve well in reasonable thicknesses. Both of the above-mentioned external stiffeners present the distinct disadvantage of locally increasing the catheter's O.D. and thereby limiting useable, already precious wall thickness through the length of the catheter. Inasmuch as the epidural needle determines the largest diameter that will pass, the diminished wall thickness available imposes further limitation on the combined thickness of external tubular covering(s) and the thickness of any helical reinforcements. Decreasing these only slightly greatly diminishes the maximum internal pressure, overall strength and kink resistance of the catheter.

Samson teaches methods of catheter stiffening in several U.S. patents pertaining to interventional radiological catheters. These neurological and peripheral vascular devices, which are far more procedure specific and intricate than epidural catheters, are less burdened with cost constraints and therefore need not be made by continuous methods. In U.S. Pat. No. 6,258,080 and others previous Samson teaches the use of spiral, coaxial ribbon stiffeners, spiraling in one or both spiral directions, either uni- or multifilar, and of various widths wound upon an inner tubular liner before applying the outer coating. In U.S. Pat. No. 6,090,099 a metallic braid lies between at least one internal stiffener member and the exterior tubing member. Although the inner stiffening tubing is of length and wall thickness similar to those in the present invention, they are made by a method of construction which is entirely distinct, being built individually from within upon a mandrel, the outer cover being applied last by heat shrinking, utilizing mostly radiation crosslinked polyolefins. Furthermore, the melting point of the inner stiffening tubing is about equal to the shrink temperature of the exterior tubular member. The costs of these methods of construction are also simply too great to be useful in the production of epidural catheters.

Truckai, et. al., in U.S. Patent teaches a deflectable electrophysiology catheter with a flexible stiffener member sliceable within an axial lumen to be used to control catheter stiffness.

Racz, in U.S. Pat. No. 5,899,891 teaches a catheter structure utilizing a coil or other flexible means for increasing a tube's end strength adhered within either the proximal or distal end acting as an anchor for an axial cord laterally mobile within the catheter. These end modifications can 'possibly (increase) its rigidity, but do not generally involve decreasing the tip's flexibility.' They provide generally a method to reinforce the proximal end so as to anchor the intraluminal cord, on which the catheter's tensile integrity depends.

Carter, in U.S. Pat. No. 5,599,326 teaches a structure for vascular catheters that achieves stiffness control with an interior stiffener comprising a spirally cut tubing member, where the spiral pitch may be varied, and a gap introduced between slit sections to control stiffness. Similar to the case for Samson, v.s., these catheters are constructed individually on mandrels from the inside outward.

Larson teaches, in U.S. Pat. No. 6,475,209 a catheter with a spiral cut transition member disposed within the annular lumen between inner and outer tubes.

Jansen, et al., teach, in U.S. Pat. No. 6,638,316 the use of spiral wound stiffeners, the first metallic, the second non-metallic which result in a relatively stiff proximal segment and a relatively flexible distal segment into which only the second stiffener continues.

Chow, in various U.S. Patents including U.S. Pat. Nos. 5,976,120, 6,171,296 and 6,296,631 teaches construction of a catheter with changing flexibility by using reinforcing strand (s) which changes diameter from proximal to distal end of the catheter. These variations in reinforcing strands are not economical to employ in the manufacture of epidural catheters.

Le, et al., teach in U.S. Pat. No. 6,355,027, the construction of microcatheters by the application of resins of different Shore hardness, along and about the braid which overlies an inner resin layer, thereby establishing two regions of different stiffness.

There is still, therefore, an unmet need to make a strong, economical epidural catheter based on a continuously wound and extrusion-coated structure with regional stiffening adequate to allow insertion.

OBJECTS OF THE INVENTION

Accordingly, it is the object of this invention to provide a helically reinforced epidural catheter having a constant outside diameter comprising an internally stiffened section of a predetermined length and positioned a distance certain proximal to the catheter's distal end which catheter does not require a stylet for its insertion into a patient's epidural space.

It is a further object of this invention to provide a stylet-free epidural catheter, which is economical to produce, stiffened regionally from within its lumen.

It is a still further object of this invention to provide a flexible tip catheter which is reinforced in a limited length back from the tip with a thin length of stiffening plastic material expanded into permanent contact with the interior of the catheter tube by heat treatment after insertion of the stiffening material into the catheter.

It is a still further object of the invention to provide a method of producing a catheter with an expanded internal stiffening member to provide a stiffened portion of such catheter just back of a flexible tip.

It is a still further object of the invention to provide a method of stiffening a catheter just back of a flexible tip by subjecting a plastic internal stiffening tubular ring or cylinder to orientation or elongation under thermal influence and thereafter positioning such in the interior of a catheter near the end followed by heat treatment to cause reorientation and expansion into intimate contact with the interior of the catheter tubing in the section to be strengthened.

It is a still further object of the invention to provide a method of stiffening a catheter just back of a stiffened tip by subjecting a plastic internal stiffening ring to orientation or elongation under thermal influence and thereafter positioning such in the interior of a catheter near the end followed by heat treatment to cause reorientation and expansion into intimate contact with the interior of the catheter tubing in the section to be strengthened.

It is a still further object of the invention to provide a method and apparatus for making a stiffening material for use in the interior of an epidural catheter.

Further objects and advantages of the invention will become apparent from review of the following description and appended drawings.

SUMMARY OF THE INVENTION

In accordance with the invention a flexible tip epidural catheter is reinforced for passage through an epidural needle or cannula by a limited length of in situ expanded plastic reinforcing material positioned in the interior of the catheter removed from, but just behind, the tip, said expanded reinforcing material having been critically elongated in a tubular condition to be of a diameter which can be slid into the catheter tip and then expanded by stress relief treatment such as heat treatment to securely engage the interior of the catheter, effectively stiffening that section of the catheter without significantly increasing the fluid flow resistance of the interior because of the extreme stiffness, extremely thin wall, and relatively short length. A method of conveniently making the interior stiffening material is also provided by a careful elongation of the material by a special apparatus. A preferred continuous method of producing the interior stiffening material is provided.

BRIEF DESCRIPTION OF THE DRAWINGS

FIG. 7 is an isometric view of one end of the apparatus of FIGS. 5 and 6.

FIG. 8 is an isometric view similar to FIG. 4 with a section of tubing shown wound on the apparatus.

FIG. 11 is a diagrammatic view of the extension apparatus of FIGS. 9 and 10 being used to draw out or elongate the stiffening tube above its glass transition temperature.

FIG. 12 is a diagrammatic view of the elongated stiffening material being sectioned into lengths for passage into a catheter.

FIG. 13 is a diagrammatic view of a section of the stiffening material of the invention being inserted into the catheter and a heat treatment oven available to effect consolidation of the two into a unitary whole.

FIG. 14 is a diagrammatic view of the end of the catheter with the stiffening material therein in position to be exposed to a heat treatment.

DESCRIPTION OF THE PREFERRED EMBODIMENTS

Figure 1:
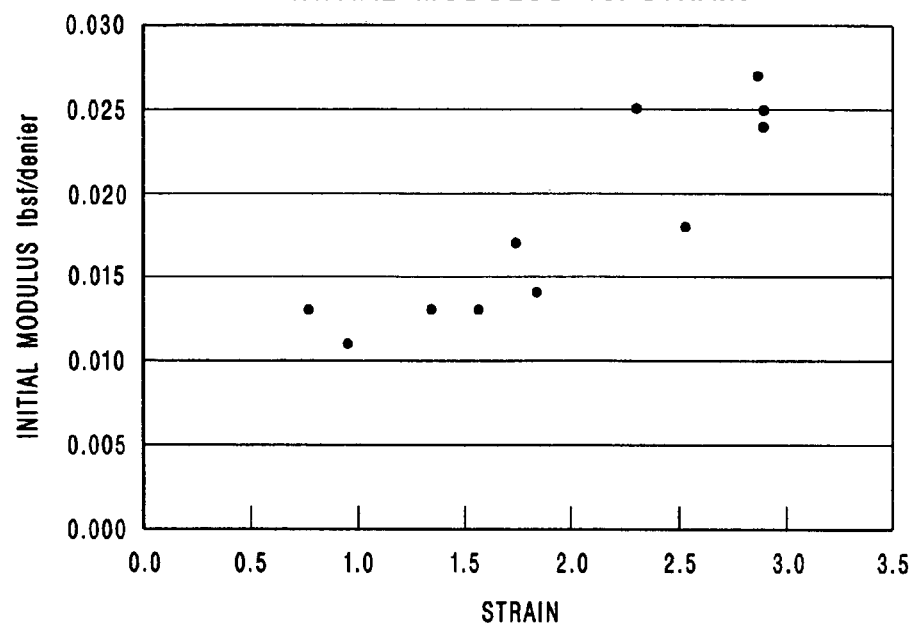
FIG. 1 is a plot of the initial modulus versus the strain occurring in a typical strengthening material.

So-called epidural anesthesia produced by the injection of a local anesthetic into the extradural regions of the spinal column, i.e. between the spinal dura mater, a dense, laminar, latticed mat of collagen and elastin fibers protecting the arachnoid membrane interior thereto as well as the spinal cord and including between them the highly vasculated pia mater membrane next to the spinal cord, and the vertebral periosteum and ligaments within the vertebral column, namely the ligamentum flavum holding the vertebrae together. (The spinal fluid circulates in the so-called subarachnoid space between the arachnoid and pia mater.) This epidural space, exterior to the dura mater and containing a quantity of loose fat and areolar tissue plus a plexus of veins, is distensible and can expand when a fluid is injected, a phenomenon which allows pressurized saline to flow into the space when the tip of the epidural needle enters, the so-called 'loss of (injection) resistance technique', after piercing the ligamentum flavum. This epidural space also allows anesthetic fluids to migrate to adjacent vertebral levels and to move outward along emerging peripheral nerve roots, thereby desirably broadening the anesthetic effect. Anesthetic also migrates into the subdural space and spinal cord within, so as to act directly upon the spinal cord, but the effect is more slowly manifested than with direct spinal injection. Larger volumes of anesthetic are required so that it can bathe larger areas such that anesthetic concentrations within the cord can be more quickly and broadly achieved. Disastrous consequences, however, can result if the venous plexus i.e. the system of venous vessels draining the epidural space, is penetrated and the charge of anesthetic is accidentally injected directly into the vascular system where it is very quickly transported to other parts of the body and may cause undesirable consequences up to and including cardiac arrest.

With the development of very thin plastic catheters having insufficient stiffness or rigidity, particularly at the tip, to puncture or penetrate the epidural venous plexus, the danger of such penetration has been essentially eliminated or dramatically reduced. On the other hand, the lack of stiffness of the catheter has created a further problem in that the then very flexible catheter material is difficult to advance from the epidural needle by and through which the catheter is introduced into the body and between the vertebra through the tough ligamentum flavum and into the epidural space without the use of a so-called stiffening stylet. Trivially small forces are needed to pass the catheter through the epidural needle and even through the needle's curved tip. Passage of the catheter's tip into the epidural space, however, requires nonzero force to push the catheter tip forward into the diffuse areolar tissue and loose fat and amidst the venous plexus and distal lymphatic vessels within the epidural space. The section of catheter being pushed into the proximal end of the epidural needle as the tip of said catheter is emerging from the needle's tip must therefore be stiffened so that it can be advanced, its column strength allowing force exerted on it by digital manipulation to be transmitted to the catheter tip by the intermediate catheter material longitudinally movable yet radially constrained within the epidural needle. Various suggestions for creating such stiffening have been advanced as disclosed in the prior art. However, none of these prior suggestions have been particularly successful for various reasons.

The present inventor has now discovered that the necessary stiffening of the proximal portions of a flexible tip catheter can be very effectively created by inserting a very critically elongated length of longitudinally stretched tubing into the end of the main catheter tube and heat treating the catheter material to cause the component plastic of such elongated section of tubing to return or 'contract' toward its original dimensions, thereby at least partially expanding laterally and establishing close contact with the internal walls of the main catheter tubing. This will sufficiently stiffen the section of the catheter so it can be pushed into the needle or cannula but will leave the unstiffened flexible tip all without significantly restricting the fluid conductivity of the catheter. The inventor has also designed an apparatus and method for producing the critically expanded tubing prior to introducing it within the catheter followed by heat-treating to expand into intimate contact with the walls of the main catheter tube.

The present invention provides a style-free epidural catheter comprising an elongated tubular member having a proximal end, a distal end and a longitudinal extent, the elongated tubular member including an outer tubular cover and at least one helical reinforcing member, said elongated tubular member defining a lumen therethrough; said catheter further comprising a predetermined length of a thin-walled stiffening tube placed within the lumen of said elongated tubular member and in close conformation with said at least one helical reinforcing member, said stiffening tube being placed a predetermined distance proximally from said tubular member's distal end, said predetermined distance and length derived simply from the length of epidural needle to be used for insertion and desired maximum depth of catheter placement. The close conformation between said elongated tubular member and the stiffening tube affords synergistic benefits: the elongated tubular member prevents kinking of the thin-walled stiffener within, while said stiffener girds the elongated tubular member further against radial collapse in the very region which, in use, requires such support most. Presence of the stiffener not only provides adequate column stiffness to allow the catheter to pushed during insertion, but also provides a locally higher modulus in tension for digital manipulation of the catheter or to remove it from pinching in vivo. This method of stiffening has the further advantages of having no effect on the smooth, uniform outer diameter of the catheter and of providing further tensile stiffening with no additional external roughening in the event the epidural catheter proves difficult to remove. The preferred embodiment achieves close conformation between said stiffening tube and said elongated tubular member by manufacturing said stiffening tube from oriented material which, when heated, expands diametrically and by placing said stiffening tube into said lumen and applying heat so as to expand said stiffening tube onto the inner diameter of said helical reinforcing member. The chemical physics and manufacture of such 'heat-expanding' tubing is disclosed hereinafter.

Figure 5:
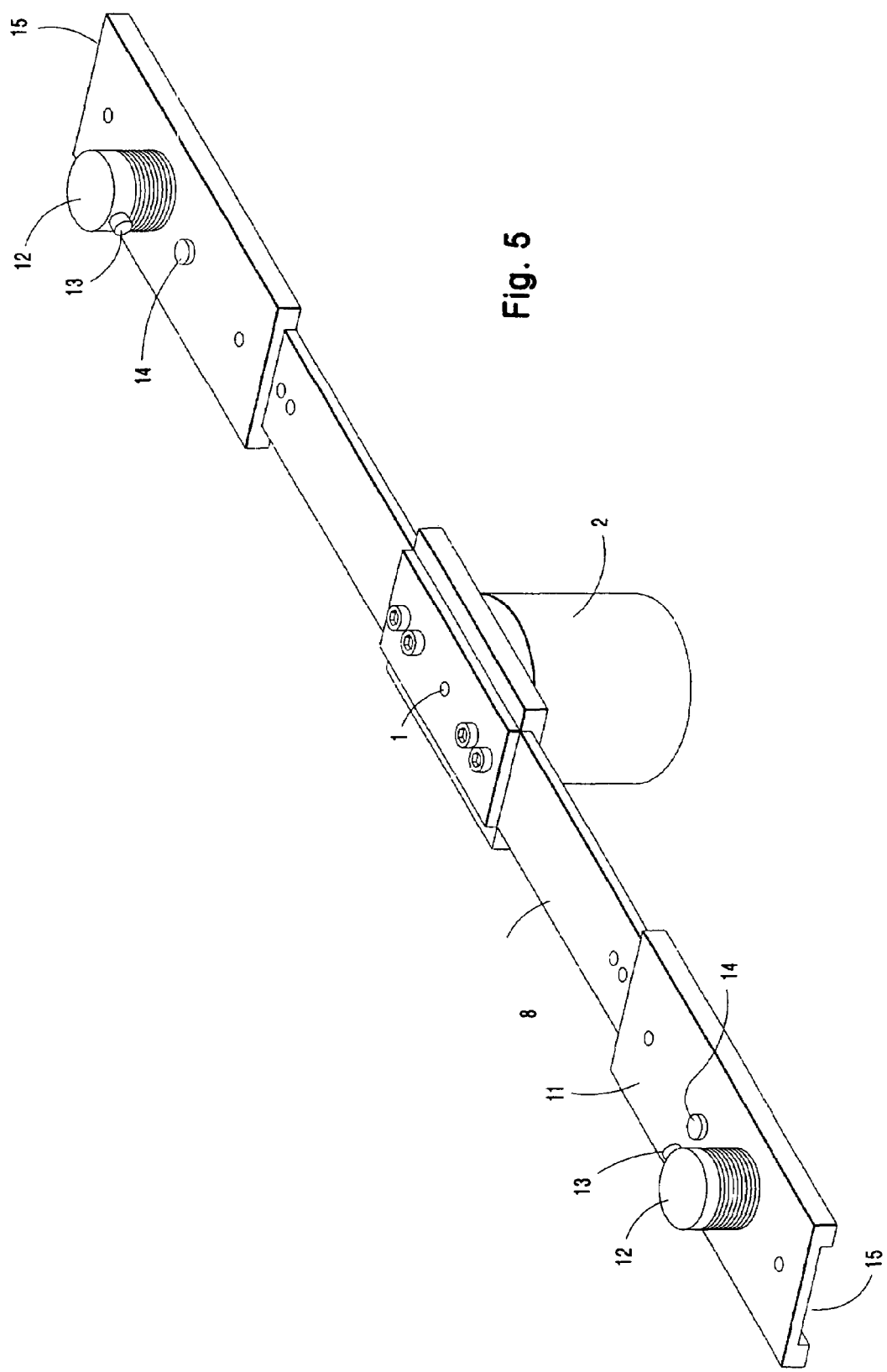
FIG. 5 shows an isometric view of an orienting apparatus in accordance with the invention.

Stiffening the catheter from within the lumen requires a thin-walled tube of a material with high Young's modulus, since the cross section moment of inertia, I, is so minute, high total elongation lest it be brittle, and good elastic recovery from a considerable strain of several per cent lest it be easily bent. A high Young's modulus E, is less critical on the outer diameter, since I, for a thin-walled tube of wall thickness t, varies as the cube of the tube diameter times t, effective stiffness varying as the product of E and I. Equivalent stiffening to that of an internal tube or coating, therefore, can be had with a thinner layer, or with a material of lower modulus E. An external element would have to sustain higher recoverable strain and would be more likely to distort permanently from its intended straight condition. A further disadvantage of using a stiff, thin tube on the outside of a flexible spiral reinforced tube is that when elongated, the coil and tube will, at high elongations, shrink in diameter faster than the external stiffening tube, pulling free from the inside of the thin-walled stiffener. FIG. 5 of U.S. Pat. No. 5,947,940, included herein by reference, compares diametrical shrinkage of wound coils of various length ratios to shrinkage of an elastomeric tube with Poisson ratio 0.5. An oriented stiffener tube will have much lower Poisson ratio and its diameter will shrink more slowly with elongation. Coils within such a stiffening tube will therefore decrease more rapidly in diameter and will pull away from this external stiffener leaving the stiffener tube behind at large diameter, unsupported and vulnerable to catastrophic collapse. Only if the thin-walled tube or external coating is strongly adhered to the reinforced tubing will this not occur. The full tensile load will then be born by the stiffening tube until it fails in tension, whereupon these external fragments may create a rough external surface complicating extraction.

An external stiffener must not be too stiff, lest it require strain relief features at its ends or have difficulty passing through the epidural needle's curved tip. In order to meet this stiffness limit, inasmuch as its stiffness follows its thickness times the cube of its diameter, it is possible for an external stiffening tube to be thinned so severely that its cross section area, which determines its tensile strength and increases only linearly with diameter and thickness, will be inadequate. When the stiffening element is internal on the other hand, its wall thickness is necessarily greater to achieve its stiffening effect at the smaller, inner diameter. The small, internal stiffener must therefore have a greater cross section area and will have tensile strength greater than that of an external stiffener of the same material and stiffness.

Epidural catheters must, most commonly, pass fluid only. The catheter's fluidic resistance is the sum of the segment's resistances acting in series, plus any transition effects. The stiffener's presence has an effect upon fluid conductivity which is 'weighted' by the short stiffening lengths involved, usually 5-10 cm, only about 6-12% of total flow path length. Even if an especially small I.D. stiffener is needed to achieve adequate stiffening or is desired so as to increase said stiffener's tensile strength, the total fluid resistance increases only slightly. When the catheter is loaded to tensile failure, the internal stiffener is radially compressed and integrated into the collapsing spiral coil and outer tubular cover, further strengthening the catheter. Even if the total elongation of the stiffener is less than the length ratio of the spiral reinforcement, the fragments into which the stiffener breaks have only trivial effect on the outer diameter of the collapsed catheter and do not complicate its removal.

Of foremost importance for providing effective stiffening is the high modulus achieved when all of the polymeric chains of the plastic material are largely parallel and not randomly directed. Elastomeric, rubbery behavior is a property, which derives from the statistical mechanics of a polymeric chain with complete rotational freedom around every linkage. When those chains are stretched taught and preferentially held in that configuration by intermolecular forces, polymers can achieve some tremendously high tensile properties as it then depends upon the extremely high strength and moduli of the molecular bonds themselves. It is such orientation in Kevlar, Spectra, Vectran and the like that stops bullets or enables Mars landings. Other high modulus material develop their properties because of a natural tendency to have highly aligned polymer chains. Polyimide, for example, is prisdisposed to this oriented structure because of a backbone with para-linked benzene rings. The flat, unsaturated rings tend to stack and the para linkages are directly across from each other on the six membered ring. PEEK is another linear, aromatic polymer with high moduli and liquid crystal polymers, LCPs, have inherently oriented crystalline structures with high tensile stiffness. It is possible to make thin-walled tubes from these materials, even to very small and precise dimensions, and, in at least one embodiment of the current invention, to place them within the lumen of a catheter. In one possible embodiment of the invention, local stiffening of a helically reinforced epidural catheter can be achieved if said helical reinforcement is in a single spiral direction as is preferred. By twisting a predetermined length of the distal end of said epidural catheter, its inner diameter can be increased as the reinforcing coil is 'wound open.' A predetermined length of thin-wall stiffening tube can then be inserted before releasing the 'expanded' catheter, whereupon the stiffener will be engaged by the shrinking inner surface of said catheter as the twist is elastically reversed. In another possible embodiment, the stiffener tube can be inserted into said spirally reinforced epidural catheter and contacted by the catheter surface by elongating and or twisting the catheter. The reduction of the inner diameter, which accompanies this twisting and/or elongation then, causes the catheter tube itself to engage the stiffening tube. Annealing this twisted/elongated assembly can allow this smaller diameter condition to be or. constitute a new equilibrium condition of the catheter. In still another possible embodiment, a stiffening tube is simply positioned within the lumen of the catheter, and anchored at its intended location by adhesive means, including the application of a heat-activated coating to the outside surface of said stiffening tube. The high tensile and flexural moduli of the oriented stiffener tubing within the lumen of the catheter are the critical elements of the invention, not whether orientation needed to achieve these moduli has been heat set during drawing (and immobilized with adhesive) or only after placement (thereby not requiring adhesive). A combination of heat setting and heat activated adhesion can be used, but will normally not be necessary if there is sufficient heat activated expansion of the stiffener in accordance with the present invention.

In the preferred embodiment, the internal stiffener comprises a thin-walled tube of oriented, heat-expanding polyester, most preferably polybutylene terephthalate, PBT or polytrimethylene terephthalate, PTT, two polyesters known for their ability to recover elastically from high strains. Polyesters as a material family are highly chemically inert and well suited for medical use. The phenomenon of heat shrinkage relies on heat stabile crosslinking. Typically, a polymer is crosslinked by radiation or chemical means to achieve intermolecular bonds that provide the 'return-force' pulling a tube, for example, back toward its original dimensions. What is really convenient about polyesters is that orientation induced crystallization accomplishes this end without the need for a separate cross-linking step. Strain induced orientation aligns the polymer chains which then associate on a intermolecular level to form crystalline structures which act as physical cross-links. Unless these structures are stabilized, 'heat-set' by annealing under tension at temperatures near the melting point, there is a tendency for the oriented, crystal-crosslinked material to shrink back toward its original shape on heating, the crystal crosslinks melting and allowing the chains to disorient, returning toward their original configuration. Heat shrinking is commonly applied to uni- and biaxially oriented films and to tubes inflated so as to later shrink around something placed within them. This patent is the first example known to the inventor to use 'heat shrink' technology to apply a tube to the inner lumen of another. It is relatively easy to achieve longitudinal shrinkage of about 10% with accompanying diametrical growth of 5%, sufficient to allow simple insertion of a thin-walled tube into position within the catheter and to have it engage the I.D. during 'shrinkage.' Addition of a heat-activated adhesive layer on the outside of this 'heat-expanding' tubing can assist in anchoring the stiffening element as noted above. Alternatively, inclusion of short tubular segments of a low melting point polymer to fuse and establish 'stops' on one or both ends of the stiffener can achieve the same constraint.

Although monofilament technology uses a continuous drawing process to achieve the exceptional tensile properties which result, the initial extruded solid or tubular preforms, usually in significant numbers, are extruded vertically downward from a multiorificed spinneret into a water bath. These quenched amorphous preforms are then drawn, or oriented, continuously by passing through or between two godets operating at different lineal speeds with a heated region between. Godets are sets of usually odd numbers of corotating cylinders arrayed in two horizontal rows. Because the filaments weave halfway around each cylinder, then pass to a cylinder in the other row, pass halfway around it and return to the next cylinder in the first row, and so forth, the cylinders effectively grip the filaments on the cylinders or rotating frames and thereby define the lineal speed of the filament through the godet. The filament in the region between the two godets is heated above the glass transition temperature of the material, a temperature at which the amorphous preform softens substantially and quickly elongates, yielding before the cooler, much stiffer material immediately before and after the heated regions. The 'drawing' that occurs in this heated region by virtue of the difference in initial and final godet speeds introduces molecular orientation while dramatically thinning the filament. Though such monofilament lines can produce many ends simultaneously and can achieve complex and intricate 'solid' cross sections, hollow cross sections are limited to simple, relatively thick-walled and relatively imprecise hollow fibers. Though it is conceivable to practice the current invention using a stiffener that is not tubular, the extruded three or four cross shape would impose much higher viscous drag within the lumen, because of having much higher surface area where the fluid velocity is restrained. The DuPont Company, for example, has recently begun making a so-called trilocular structure or shape filament for use in paint brush bristles in which there is a bracing network of plastic walls meeting in the center to brace the extruded bristle against buckling. The preferred embodiment of the current invention requires substantially thinner and more uniform walls and has the potential to realize beneficial properties from more complex tubular profiles unattainable on most current monofilament lines.

In addition to using a thin-walled tubular insert to stiffen the catheter, it may be advantageous to consider other internal stiffeners of other shapes, which do not occlude fluid flow if they kink during severe distortion. Though the cylindrical stiffener of the presently described embodiment maximizes stiffening effect while simultaneously maximizing hydraulic conductivity, it does suffer the disadvantage of possibly occluding flow when and if buckled. To ameliorate this possible problem one can employ the same approach as disclosed by Antoshkiw in U.S. Pat. No. 5,776,115 assigned to Becton Dickinson and Company (Ribflex patent). That is, one can adorn the inner surface of the stiffener with longitudinal ribs in odd number which prevent total occlusion of the lumen by maintaining patency through small peripheral conduits 28 which cannot collapse even though the main fluid channel 29 may have. Though these inward radial ribs interfere with fluid flow and decrease the hydraulic conductivity of the lumen, this effect is tolerable when only expressed over the limited length of the stiffener. Such full-length ribs had a deleterious effect on the flow through the B-D Ribflex catheter. A further embodiment comprises a stiffener tube made such that, when severely distorted, longitudinal tearing occurs, thereby 'opening' pathways for the fluid to flow past the kinked or torn region. For example, if the regions between the radial ribbing were so thin as to split easily on kinking, or if there was a linear weakness along the length of the stiffener that achieved the same splitting effect, these linear ruptures would restore catheter patency. The extruded stiffener need not be tubular. It could very well have an array of three or more thin plates emanating radially from the central axis in a starburst pattern a la the DuPont trilocular arrangement mentioned above. Though offering higher hydraulic resistance, with more flow impeding material arrayed close to the neutral axis and thereby contributing much less to the cross section's moment or inertia, I, and its stiffness, such non-tubular shapes would not occlude flow when contorted.

Extrusion lines for miniature tubing can achieve these more demanding preforms, but can neither achieve the drawing needed for enhanced properties nor easily attain the smaller dimensions which require much smaller tooling, finer melt filtration, and much smaller extruders to minimize residence times and polymer breakdown within the extruder's heated barrel. Furthermore, simply marrying existing godets with a miniature tubing line may prove inadequate. In order not to distort or collapse the thin-walled preform and drawn stiffener tubing, the godet's cylinders' surfaces will undoubtedly require 'U' or 'V' groove(s) in their surfaces so as to support the tube against collapse as it passes the point of tangency where tension is applied to effect drawing and orientation in the heated zone between godets. The cylinders would also benefit from a larger diameter for this same reason. Current godets have smooth surfaces without support grooving and small godets for laboratory monofilament lines, which recommend themselves as of appropriate size and power, have cylinders smaller than the inventor believes prudent for handling very thin-walled tubing.

Given the lack of available equipment, before capitalizing and experimenting with a new extrusion/drawing process, an intermediate process was developed where the thin-walled amorphous preform is extruded and spooled on a conventional tubing line and the drawing process is achieved in a separate 'batch' process. The preform tubing is served around parallel pins spaced perhaps 50 cm apart on a fixture that elongates the tubing by separating the two, still parallel pins to a vector distance orthogonal to their centerlines and of length three to four times their original separation. The regions of the tubing in contact with the pins must be discarded, while all the tubing between them will be uniformly elongated. This deformation is best done at a temperature above the material's glass transition temperature, $T_g$, a second-order phase transformation best characterized by differential scanning calorimetry, that results in a substantial drop in moduli which allows the drawing to occur uniformly and gradually along the entire heated length. Below $T_g$ the 'drawdown' occurs completely, up to the so-called 'natural draw ratio' in certain regions before others, these regions then growing in length to consume the entire length of the sample. Furthermore, the tubing typically deforms and whitens at these lower temperatures. Above $T_g$, as the tubing elongates, its diameter is a simple function of strain, as taught in the U.S. Pat. No. 5,947,940, the ratio of diameter to initial diameter is equal to $1/(1+\text{epsilon})^{1/2}$ where epsilon is strain which equals (length-initial length)/(initial length). The lumen of the tube obeys the same relationship and the wall thins slightly as the tubing is stretched. For PBT (polybutylene terephthate), the processing temperature is only 45 degrees Centigrade.

Figure 2:
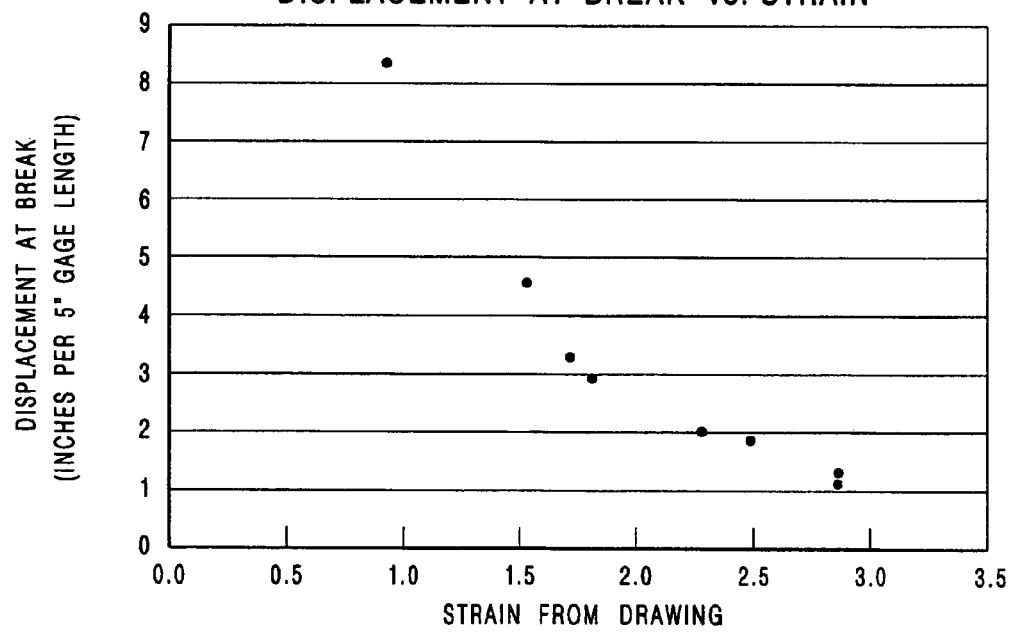
FIG. 2 is a plot of the strain in the strengthening or stiffening material versus displacement at break of the material.
Figure 3:
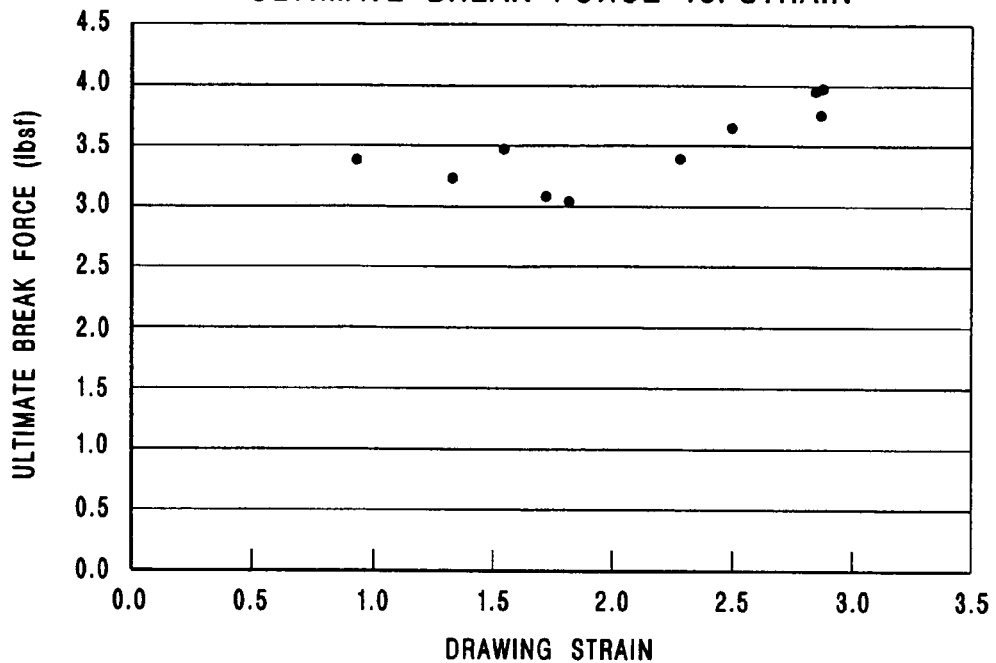
FIG. 3 is a plot of ultimate break force of the strengthening material versus the strain in the material.
Figure 4:
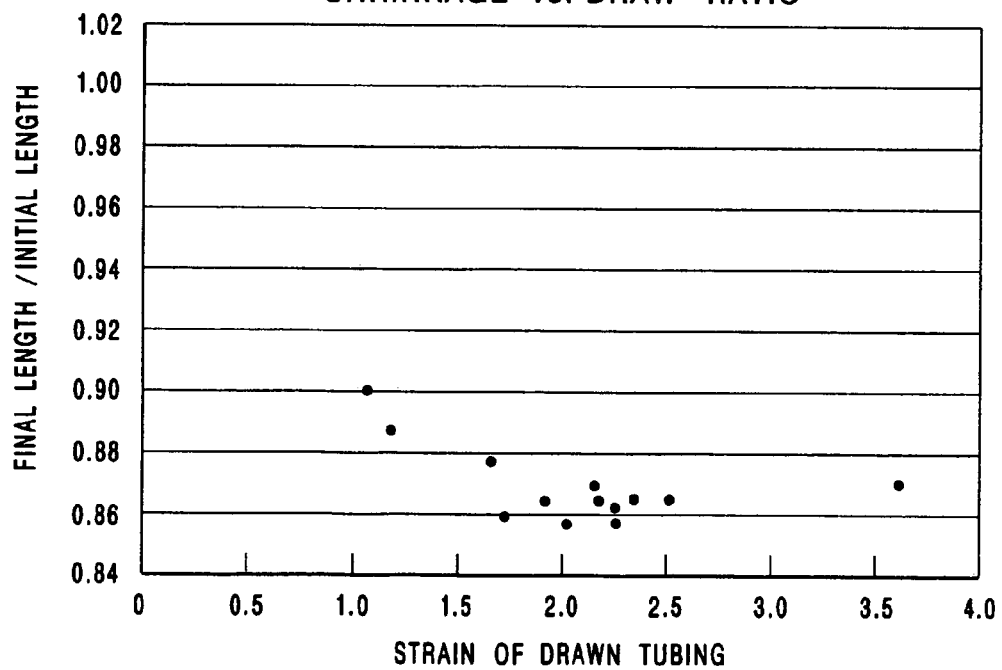
FIG. 4 is a plot of the shrinkage versus the draw ratio of the strengthening or stiffening material of the invention, i.e. the final length after elongation versus the initial length plotted against the strain of the drawn tubing.

When one performs tensile testing on 'heat-expanding' tubing with varying degrees of drawing orientation, one learns that the initial modulus increases with the degrees of orientation (FIG. 1), that the ultimate elongation of the drawn tubing decreases with increasing orientation, i.e., increasing draw ratio or drawing strain (FIG. 2), but that the ultimate strength of the tubing is a relative constant (FIG. 3) across different draw ratios, consistent with the mental image of the drawing and later tensile testing as stretching out a fixed, limited amount of natural 'slack' in these polymers. When examining the degree of shrinkage at 110 C versus the draw ratio of the tubing (FIG. 4) one notes that it does not decrease much with lower draw ratios. These facts allow one to tailor the properties of the stiffening tubing, trading decrease of initial modulus (stiffness) in return for increase of ultimate elongation. Given small variations in the dimensions of the amorphous extruded starting tubing, one can precisely control the critical final O.D. by slightly varying the draw ratio without causing significant changes in important properties. There is no strong dependence of tube properties on precise drawing temperature and only minimal degradation of available shrinkage was seen when the drawn tubing was not removed immediately from the warm water drawing bath. This last experiment shows that the process can be run in a warm air oven.

In the preparation of a catheter having the integral stiffening insert of the invention, such insert is initially formed as described above of a thin-walled tube of oriented, heat-expanding polyester, preferably PBT or PTT known for their ability to recover elastically from high strains. Such thin tubing must be very accurately elongated without overdrawing and in order to do this the inventor prefers to wind a length of tubing on a pair of capstans at a fair distance from each other and then by suitable apparatus move one or both capstans away from the other until the plastic tubing has been elongated by a factor of three or four while held at a temperature above the glass transition temperature of the plastic. Since elongation is rather severe and the plastic has a rather low ultimate strain, if the tension necessary to achieve such ultimate elongation was applied directly at any point along a length of tubing, such tubing would promptly fail and fracture at any point at which the full load was applied such as a tie point or isolated attachment point. Consequently, in order to apply a high uniform tension and attain a high uniform extension over a length, it is necessary to effectively secure or hold the ends of the tubing over an extended length. The inventor, therefore, winds the ends of the tubing onto grooved drums or capstans securing only the extreme outer ends at a fixed point shielded from stress by a last passage over the capstan. Thereupon, the grooved capstans are moved apart by a steady pull. The friction between the tubing and the capstan surface thereby spreads the tensile load along the length of contact with the capstan so that the full load is not applied at any particular point and the length of tubing between the two capstans may expand or elongate equally all along its length between the capstans without placing any concentrated stress upon a single point. The elongation is obtained by moving the two capstans apart by a predetermined distance. At the same time, the length of tubing wrapped upon the capstans are stretched to various degrees depending upon the friction with the surface from very little at the tie point beyond the capstan and progressive increasing along the capstan surface to the area between capstans where the elongation is controlled to be that desired in order to obtain the degree of elongation required. When the tubing between the capstans has reached the desired elongation, orientation and diameter, the extension between the two capstans is halted and the length of carefully expanded tubing between them is severed and then again severed into separate short lengths equal to the length of tubing it is desired to insert into the end of each partially completed length of catheter tubing. These short lengths are then placed over or upon a very thin mandrel and inserted into the end of the catheter tubing and after being positioned exactly in the section of catheter it is wished to stiffen the catheter is exposed to heat treatment upon the application of which the short stiffening member will be partially relieved of its elongation strain and will expand toward its former diameter closely contacting and becoming wedged against the insider of the catheter reinforcing and stiffening such section of catheter. While the short length of stiffening material does effectively also narrow or decrease the inside diameter of the catheter, this narrowing is only for a relatively short length and does not seriously impede the flow capacity of the catheter as a whole. Meanwhile the end sections of the thin tubing originally lying against the surface of the capstans and stretched or elongated to varying lengths lesser than the desired elongation of the stiffening material may be discarded.

The thin tubing may be conveniently loaded onto the individual capstans by providing for mounting the support for the capstans on a rotational or rotation imparting device such as a conventional winding device or the end of a lathe or the like in a horizontal orientation and rotating the support or base of such capstans so the tubing is wound by rotation of the entire support for the drums or capstans on the rotation or winding device. The support for the capstans is made in two preferably telescoping sections so that such sections can be either immobilized with respect to each other or may be slid outwardly with respect to each other preferably in a telescoping manner. The two sections are immobilized with respect to each other while the thin preform tubing is wound consecutively upon the two capstans and secured on opposite sides of the capstans and are then after winding of the tubing on the surface of the capstans disconnected-so that the section with one capstan can be moved longitudinally along the base moving the two capstans apart with a steady movement by a pressure or tension imparting device. In this manner an exact amount of tension and an exact amount of elongation can be distributed along a predetermined length of tubing by moving the one capstan base member laterally away from the other a preset distance while exposed to a predetermined temperature. A predetermined elongation of a section of stiffening tubing is thus obtained for severance into individual section for insertion within the overall catheter and expansion by appropriate heat treatment.

As indicated in the above description, FIGS. 1 through 4 are plots of the basic physical properties of plastics used in the present invention which are taken advantage of in manufacturing the stiffened epidural catheter of the present invention.

FIG. 5 then shows an isometric view of a batch-type orienting fixture generally designated as "a" ready to be loaded with extruded preform tubing. The fixture is bilaterally symmetric about its central axis, defined by a ¼-20 tapped hole 1, which as shown in this view has attached to one side a 2" diameter cylinder 2 secured by means of a ¼-20 screw. Such cylinder 2 allows the entire fixture to be temporarily mounted for rotation onto a 1" rotatable shaft about which the fixture can be spun to facilitate loading of the preform tubing upon first one or two posts or capstans 12 and then upon the other with a free length of tubing extending between the two. Such free length of tubing can then be stressed by extension by moving the capstans 14 away from each other in a manner explained hereinafter.

Figure 6:
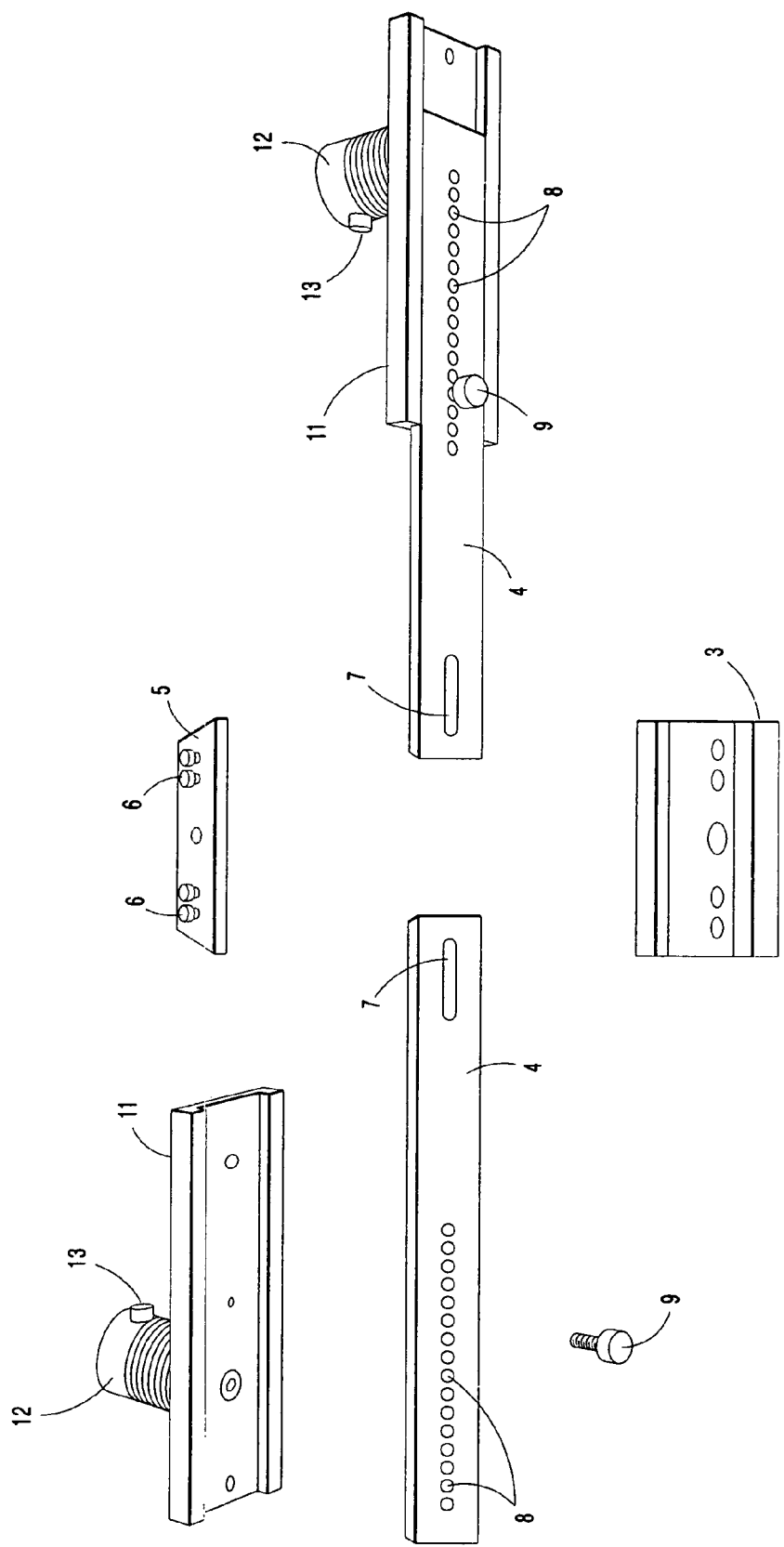
FIG. 6 is an exploded view of the apparatus of FIG. 5.

FIG. 6 is an exploded view of the orienting fixture shown in FIG. 5. A central plate 3 is grooved to received two ⅛"×1" rectangular bars 4, and has threaded holes allowing a clamp plate 5 to be attached thereto with cap screws 6. Splines 7 on the inner ends of the bars 4 allow for a small range of adjustment of the bar positions. Coarser adjustment, in increments of 0.250", is accomplished by choosing one hole from a line of holes 8 through which a thumb screw 9 engages and secures a grooved plate 11 to the bar 4 by entry into a tapped hole 10. These two adjustments allow the initial length of each half-loop of tubing, as well as the distance between points of tangency to each post 12, to be set. FIG. 8 shows the top surface of the fixture onto which two circumferentially grooved posts 12 or capstans are affixed. Such FIG. 8, plus FIG. 7 further show smaller thumb screws 13 threaded into each post 12 and thumbscrews 14 threaded into the top surface of grooved plate 11. Each plate 11 has a hole or orifice 15 near its outer end through, which said plates 11 are ultimately attached to the stretching apparatus after being loaded with tubing. FIG. 7 shows a close-up of one plate 11 with attached capstan or post 12 with thumb screw 13 which effects securing of tubing 16 to effect the process of securing the tubing ends. Thumbscrew 13 is tightened onto the first end of the tubing 16 which is looped around post 12 before being looped around the opposite post. The friction generated against the post or capstan 12 protects the clamping point under thumbscrew 13 from seeing or being exposed to the full stress during elongation. The diameter of post or capstan 12, here 1.125" (3 cm), must be sufficiently large so as to allow the tubing to be wound around it without kinking. Inasmuch as the elongation step stretches the tubing loops to large strains and high stresses approaching their ultimate strength, all efforts must be made to eliminate points of stress concentration or weakness. Mere flattening of the tubing does not produce weak features transverse to the tubing axis which might result in tensile failure; however, any buckling or kinking may cause such transverse weakness, may compromise tubing strength and must, therefore, be avoided by using posts or capstans 12 of adequately large diameter. After preferably multiple loops have been loaded onto the orienting fixture, the end of the tubing 16 is secured to the upper portion of the post 12 by clamping beneath thumbscrew 13, again after passing around the back of post 12 to allow friction to dissipate the tension seen, or generated, between posts 12 and thereby protect the point of securing the tubing 16 under thumbscrew 13 from stress which might normally cause failure, given the insult and 'stress concentration' such clamping inevitably causes.

Figure 9:
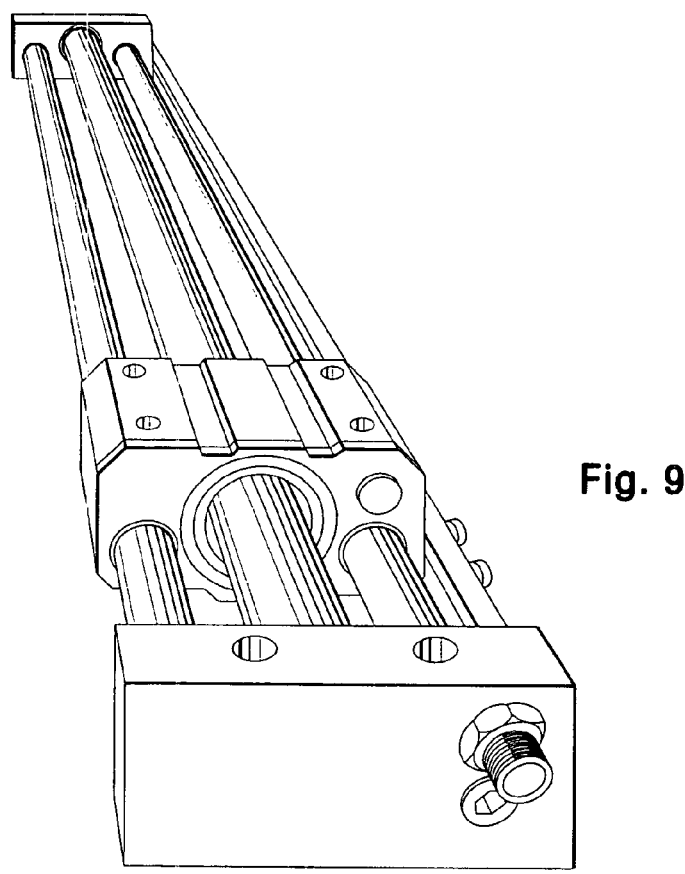
FIG. 9 is a perspective view of an extension apparatus in the form of a tubeless extender which serves to elongate the tubing used as the stiffening material.
Figure 10:
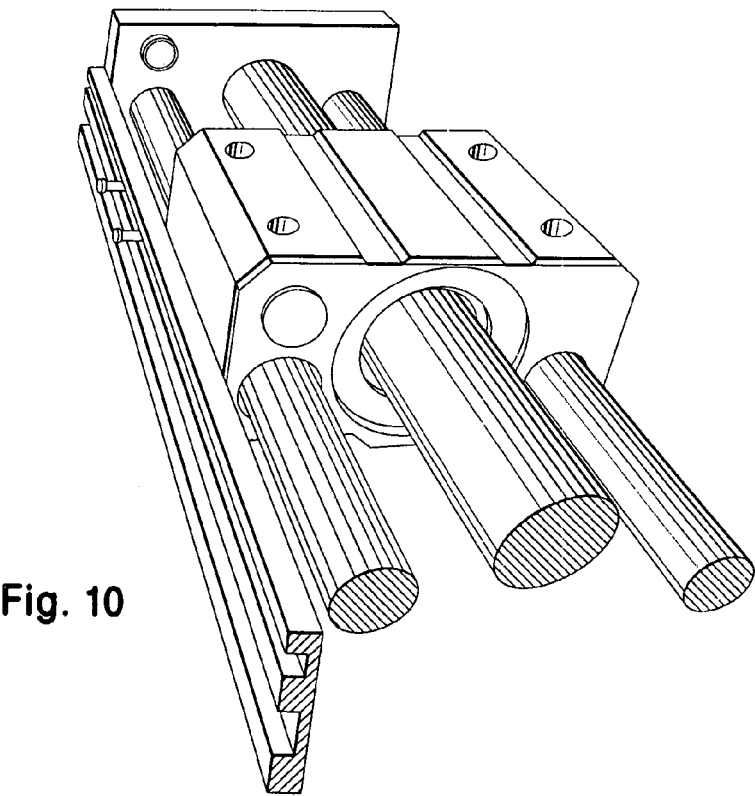
FIG. 10 is a perspective view from the opposite direction of the extension apparatus of FIG. 9.

The loaded fixture is then mounted onto the stretching mechanism, one end of which is depicted in FIG. 9, and which is viewed from the opposite direction in FIG. 10 by means of two screws passing through holes 15. One end of the fixture is affixed to a stationary platform 18 as shown in FIG. 11, while the other end is affixed to the slide of a pneumatic rodless cylinder 22. One thumbscrew 9, see FIG. 6, at this end of the orienting fixture is removed, thereby allowing plate 11 attached to the pneumatic slide 23 to move. The entire stretching mechanism "a" is placed into a warm air oven, not shown, at approximately 50 deg C. for PBT plastic and the pneumatic slide is actuated driving the slide, and one end of the orienting fixture "a" attached thereto, to its final position thereby effecting elongation of all tubing loops extending between the capstans. Final strain, ((final length−initial length)/(initial length)), is thereby controlled as needed to achieve the required tubing diameter.

Depending upon the diameters of the posts or capstans either a series of loops of tubing may be stretched between two posts or capstans 12 or a single tubing length may be elongated between such capstans or posts depending upon how many times or partial times a section of tubing must be passed over a capstan or post to bring the stress at any point below the ultimate strength of the tubing.

FIG. 11 is a diagrammatic view of the entire stretching operation and apparatus in which one end of the orienting fixture shown in FIGS. 5 through 8 with one end attached to a stationary platform 18 by a fastening 20 while the other end is attached to the pneumatic rodless cylinder 22 shown in FIGS. 9 and 10 which is also attached to a suitable support 23. As described above, the entire stretching arrangement is placed in a warm air oven at approximately 50 degrees centigrade for PBT and the cylinder is operated to stretch the loop or loops of the tubing passing between the two capstans or posts 12. As indicated above, if the capstans or posts 12 have sufficient diameter to effectively distribute any stress, multiple loops of tubing can be stretched between the posts at one time and the groove in the surface of the capstans 12 can be either helical and continuous or merely extend around the post in unconnected single grooves and multiple loops of tubing can be passed between the capstans or posts. However, if the post or capstans are of lesser diameter the tubing will be passed about such capstans several times before being extended to the next. The capstans must be of sufficient diameter so that they do not unduly bend the tubing thereby possibly causing stress, defects or even fractures.

Once the stiffening tube material has been properly oriented the elongated sections of the tubing are cut into suitable lengths to provide stiffening inserts 24 and the portions of the tubing contacting the capstans during stretching are discarded, see FIG. 12. The stiffening sections 24 are then placed on thin mandrels 26 and inserted as shown diagrammatically in FIG. 13 into the end of a previously formed catheter and the catheter end placed in a heat treating oven 28 as shown in FIG. 13 whereupon the short section returns partially to its pre-elongation orientation and expands into contact with the inside diameter of the end of the catheter away from the flexible tip of the catheter as shown in FIG. 14.

Locally stiffened flexible tip epidural catheters achieved with the batch drawn stiffener tubing shown in FIG. 11 showed highly desirable properties and justified further development of a continuous process to produce the stiffener. Even the preform tubing is fragile and is difficult to spool continuously without distortion or collapse. The discrete lengths of stiffener are very small, very stiff, and very thin-walled, and until placed within the helical constraint of the catheter lumen, are very easily kinked or crushed and are so delicate as to be a challenge to handle and feed as discrete lengths. A single extrusion/drawing process that produced the stiffener tubing in continuous lengths on a spool would, therefore, be highly desirable, avoiding the problems mentioned above.

Figure 15:
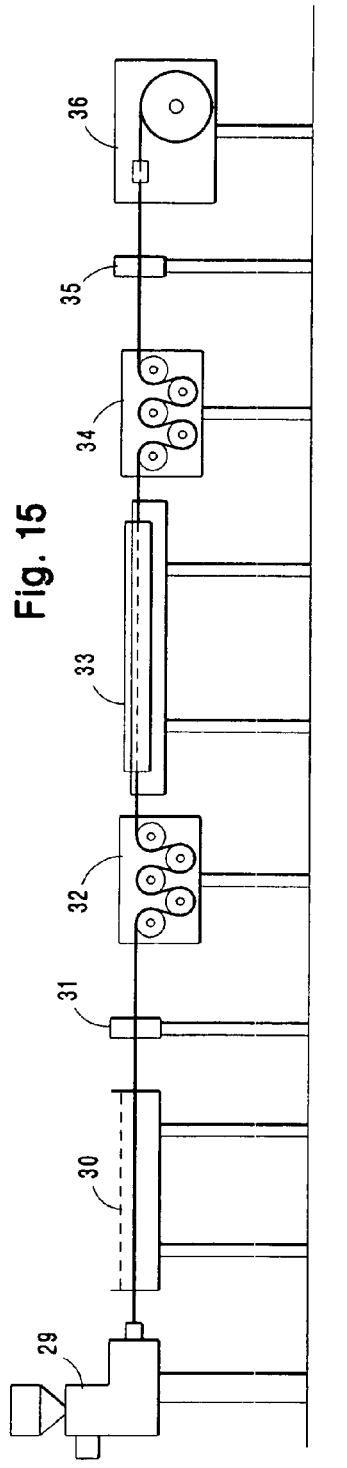
FIG. 15 is a diagrammatic view of an apparatus of the extrusion/drawing used to produce stiffening material in a continuous manner.
Figure 16:
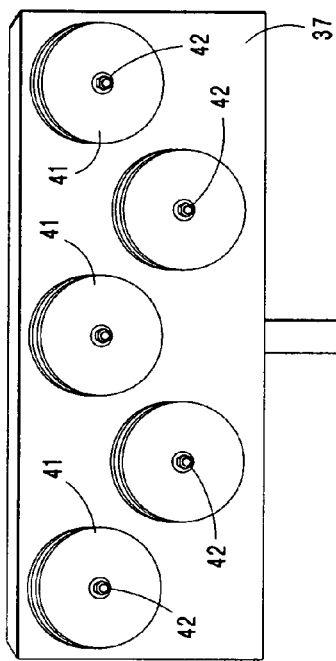
FIG. 16 is a front isometric view of a godet, as used in the apparatus of FIG. 15.

FIG. 15 dramatically depicts the various components of a continuous extrusion/drawing line, which may be used to produce the stiffener tubing of the present invention in continuous lengths. A small ½"-¾" extruder 29 with tooling and internal air pressure and screw speed controls first extrudes the preform tubing at line speed near 80 feet per minute (25 m/min) and a mass output near 1 lb/hour (0.5 kg/hr). The die diameter should preferably be near 0.085" (2.2 mm) with a die gap near 0.010-0.012" (0.25-0.30 mm) so as to produce a preform tube with 0.036" (0.9 mm) O.D. and a 0.003" (0.08 mm) wall thickness. The melt cone emergent from the extruder tooling elongates and reduces in diameter and wall thickness as it is drawn into a first water bath 30 which cools the melt quickly to prevent crystallization and preserve its disordered amorphous state of the extrudate. As the preform tubing exits the first water bath 30, passing if necessary through an air wipe to blow off water droplets, it passes through a high speed laser micrometer 31 which measures its diameter and eccentricity at sampling rates near 1600 per second so as to be capable of detecting short wavelength fluctuations in tubing diameter at the 80 fpm (25 m/min) line speed established by passage through a first godet or godet #1 identified by reference 32. FIG. 16 shows the front of godet #1 or godet 32. As the preform tubing weaves back and forth through the grooved, co-rotating godet rolls, godet #1 serves as the motive force which pulls the preform extrusion from the extruder tooling at approximately 80 fpm and as the restraint against which godet #2 designated 35 pulls at higher lineal speed to achieve elongation and orientation of the plastic tubing therebetween in the so-called drawing step. As the cooled preform tubing exits godet #1 designated 32, passing from the last of its five grooved cylindrical rolls at the point of tangency with said last roll, said preform tubing passes through a laser micrometer 31 and enters a drawing water bath 33. Although convective hot air and/or radiant heating could serve to establish the necessary hot zone, a hot water drawing bath has been found to be superior. Such a hot zone is more controllable, more uniform, and capable of much faster heat transfer than hot air, a low density fluid with extremely low heat capacity, and hot liquid also provides a much more uniform heat transfer than radiant heat transfer which depends on so many factors: for example, the solid angle subtended by the source, the albedo of two surfaces, the uniformity of the source's surface temperature and the like. The preform tubing's thin wall makes even and accurate heating critical to uniform drawing and highly recommends water immersion as the best heating means. A water bath further offers the advantage of the buoyancy of the liquid supporting the soft extrusion through the hot zone without requiring solid supports or guides, which might deform its shape. Because the drawn extrusion is so very small, however, this buoyancy is not so large as to create a floating problem such as might be seen in larger extrusions. For optimal results it is necessary that the preform tubing pass from godet #1 (32) to godet #2 (35) without touching anything solid, although gentle contact with cool extrusion means, either before said extrusion enters or long enough after it exits the hot zone, should normally be well tolerated. Tension in the line is determined by the small dimensions of the stiffener tubing and the temperature of the drawing bath 33. Buoyancy within the drawing bath 33 helps support the extrusion at the lowest point on the normal catenary shape between the two godets' support points of tangency. The ratio of the lineal speeds of godets #1 and #2, the draw ratio, determines the total drawing elongation the extrusion undergoes in its passage through the hot zone. Both godets are preferably equipped with encoder feedback such that 'electronic gearing' can be used to vary the speed of the line, to achieve correct dimensions at any given extruder screw speed, without varying the amount of orientation experienced by the extrusion determined by the draw ratio. 'Electronic gearing' refers to using feedback controlled, electronically coordinated servo motors to assure that constancy of the draw ratio is achieved depending upon the relative lineal speeds of godets #1 (32) and #2 (35). After passing through godet #2 (35), the extrusion passes onto the take-up spool 36. In order to minimize distortion, said spool should have as large a barrel diameter as possible, preferably near 14" (35 cm), and should be plastic so as to have a small moment of inertia to minimize tension variations from inertial effects. Said spool should have a padded barrel surface to cushion the extrusion from distortion from residual shrinkage pulling it against a hard spool barrel. Said spool should be carefully level wound, each revolution of spool material carefully shifted laterally on the spool so that the spool fills 'level' from edge to edge in order to minimize wrap crossings where buckling would occur. Said spool should be wound under constant tension near 100 grams force by having the spool driven through a magnetic particle or hysteresis clutch at constant torque. Take-up of the extrusion offers a challenge, inasmuch as the final line speed could be as high as 300 fpm (100 m/min). Monofilament godets can have small, soft, 'snubber rolls' which press the monofilament against the first or last godet roller to assure traction between the godet and the monofilament. This is much more difficult with the thin-walled stiffener of the present invention than normally. Some other means is needed to maintain traction against the final roller, to pull the extrusion out of the godet, and yet allow for coordinated transfer to take-up spools at full line speed after steady state conditions have been achieved and the finished stiffener tube meets specifications. Inasmuch as spools may have to be changed frequently to assure the inner tube layers are not damaged by the accumulated tension of layers above, it may become critical to be able to change spools easily without disturbing the stable extrusion/drawing process. In normal tube extrusion, line speeds are slow enough to allow the extrusion to be cut quickly and manually attached to the take-up spool. Although the extrusion/drawing process could be slowed by using a much smaller extruder, this is clearly an unattractive and problematic approach. In drawing monofilament, the quality of the level wind is usually unimportant since there is no concern for buckling at crossing points. One skilled in the art can design a take-up apparatus which employs an integral spool for taking up during startup and spool changeover, and a plastic spool of identical diameter and width held loosely on the same horizontal shaft as and directly against the integral spool by small magnets. A mechanism that allows the level-wind guides to be displaced outward and inward by a distance exactly equal to the spool width would allow one to replace the plastic spool and, just as the level wind reaches its inward limit and reverses direction on the integral spool, to move the level wind to its 'out' position. At this instant, the extrusion will quickly spool outward across the inner, integral spool and just over the plastic spool's inner flange. The level wind will then spool material onto the plastic spool from inside edge outward. When an appropriate amount of material has been accumulated, the level wind can be shifted to its 'in' position, transferring the level wind so as to spool material onto the integral spool again. A sharp blade held 'into' the slight gap between spool flanges should be easily capable of cutting the extrusion at the two points where it crosses over to and back from the plastic spool. The magnetic attachment of the plastic spool should be strong enough to achieve adequate, rather low line tension without slipping, but weak enough to be easily pulled away from the integral spool, decoupling the plastic spool without significantly disturbing the process. Upon replacing a new, empty plastic spool, the process can be repeated, allowing multiple spools of material to be collected, carefully level wound, without slowing the line to allow manual transfer to take-up spools at high final line speeds.

Figure 17:
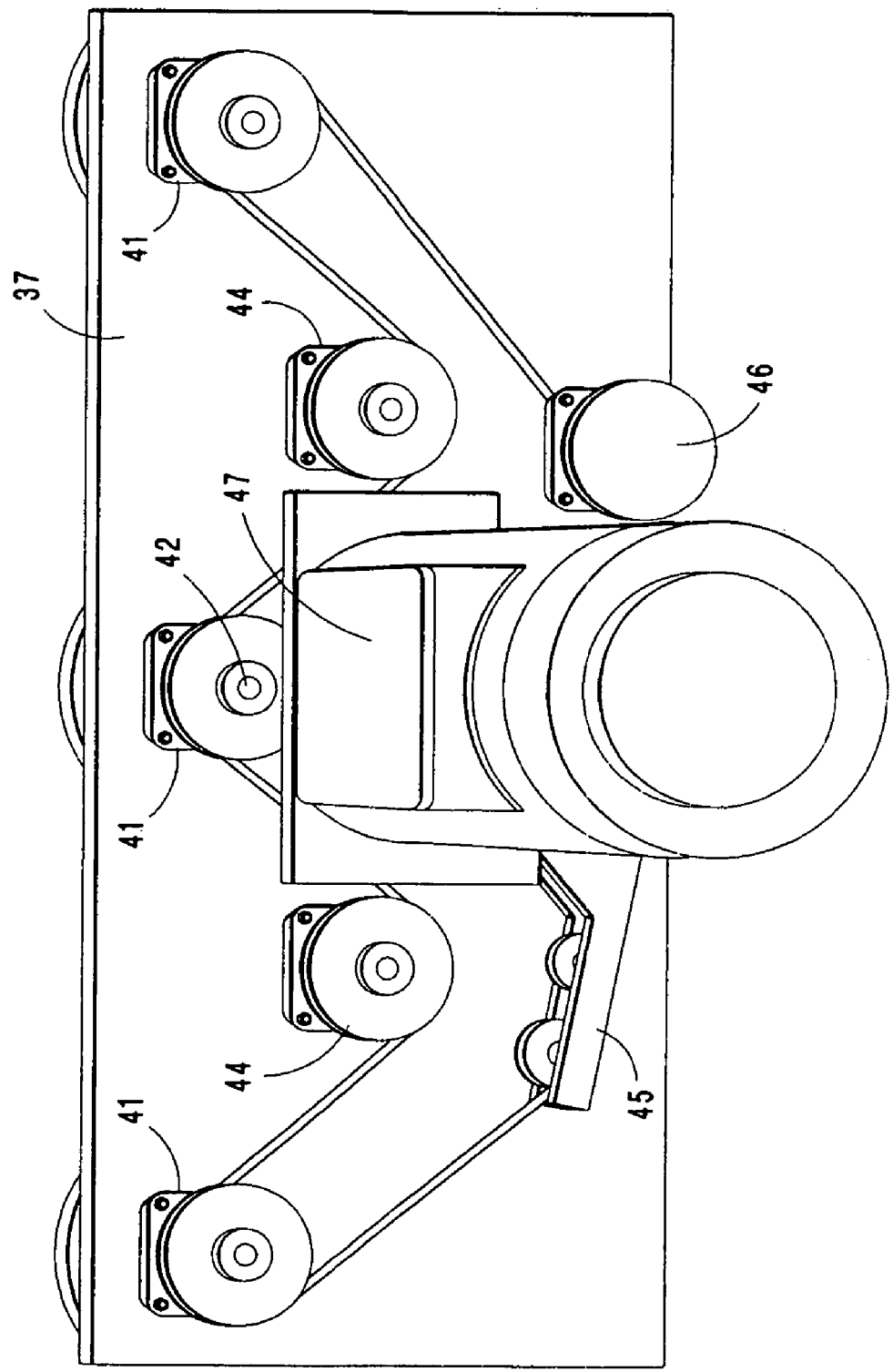
FIG. 17 is a rear view of the godet panel shown in FIG. 16.

FIG. 16 shows perceptively the front aspect of a godet used on the line shown in FIG. 15. FIG. 17 shows the rear structure of the godet of FIG. 16. Godets #1 and #2 are preferably completely identical in construction. Each consists of a vertical plate 37 mounted upon a support pole 37a rigidly attached to steel base plate 38 ultimately resting upon three adjustable feet 39. Four small, barely visible casters 40 are attached to the underside of base plate 38 allow the assembly to be rolled easily into position, the three threaded swivel pads 39 then being screwed down and locked so as to lift the base plate and create a stable, adjustable tripod foundation for the apparatus. This same base structure is used for all pieces of the extrusion/drawing line and allows for precise vertical positioning and leveling to match the working centerline heights of each individual component of the line. Each godet has five ½" (12.27 mm) ground shafts 40 held at right angles to the vertical plate, each extending through a clearance hole in the plate, using a square flanged mounted bearing on both the front 41, partially obscured and rear 41 of the vertical plate 37. On the front extension of shafts 40 are attached five godet rolls 43, cylindrical plates mounted so as to be perfectly coplanar, the groove(s) on their edge defining the tubing's path. Five L-series 24 tooth timing belt pulleys 44 are similarly mounted on the rear extension of shafts 40. The path of the double sided timing belt describes a 'W' as it passes over and under said pulleys 44, down to 12 tooth belt tensioner pulley 45 and encoder pulley 46 and over a 12 tooth drive pulley 47 mounted on the shaft of the drive motor. Angular motion of the drive shaft pulley 47 results in half that angular motion, in the opposite direction, of every godet roll 43. The arrows 44 in FIG. 16 denote identical rotation of the rolls 43 such that the preform tubing can be manually guided through the series of rolls so as engage the groove on the periphery of each roll.

Figure 18:
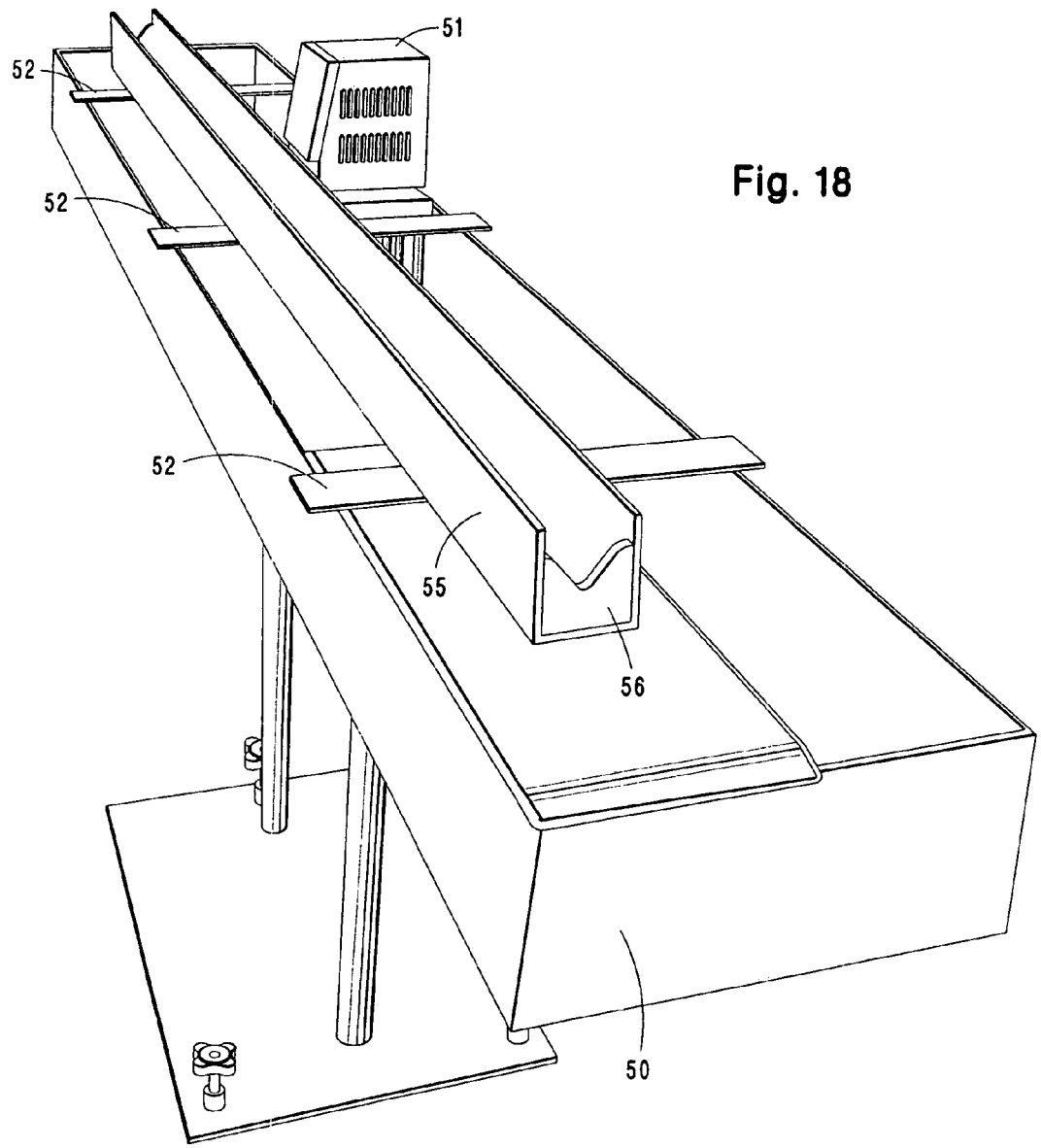
FIG. 18 is a perspective view of the drawing bath shown in FIG. 15.

FIG. 18 shows in perspective the drawing bath 33. Approximately 50 liters of water are contained in a rectangular stainless steel reservoir 50 mounted on a base 38a similar to the base 38 of a godet. The reservoir temperature is maintained at set-point by a heater/circulator 51 which pumps up to 8 liters per minute of the reservoir water through a distribution manifold 53 into a polypropylene flow channel 55 supported above the reservoir 50 on cross members 57. While the reservoir is 6'×1' (183 cm×30.5 cm) and is filled to within 1.5" (4 cm) of the reservoir top edge, the flow channel 55 is 5'×2.5" (152.5 cm×6.5 cm). Both ends of flow channel 55 are closed with weir plates 56, the most basic being a narrow V is shape. Flow from the heater/circulator 51 establishes waterfall discharge at both ends of the flow channel 55. Height of the waterfall can be calculated from flow rates and weir plate geometry. The flow channel 55 can be positioned on cross members (48) such that the waterfalls on both ends return completely to the heated reservoir 50 below.

Figure 19:
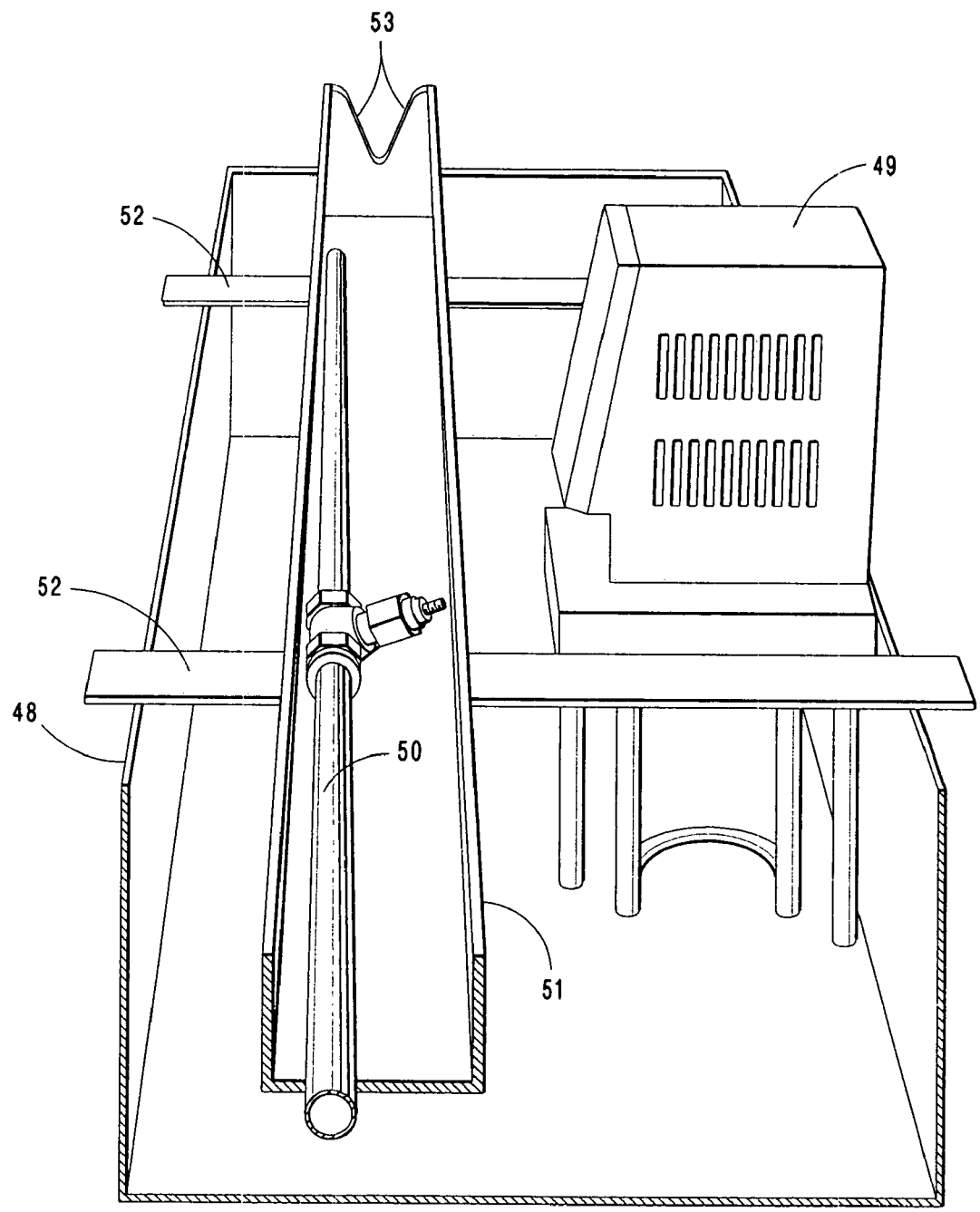
FIG. 19 is a second perspective view of the drawing bath shown in FIGS. 15 and 18.
Figure 20:
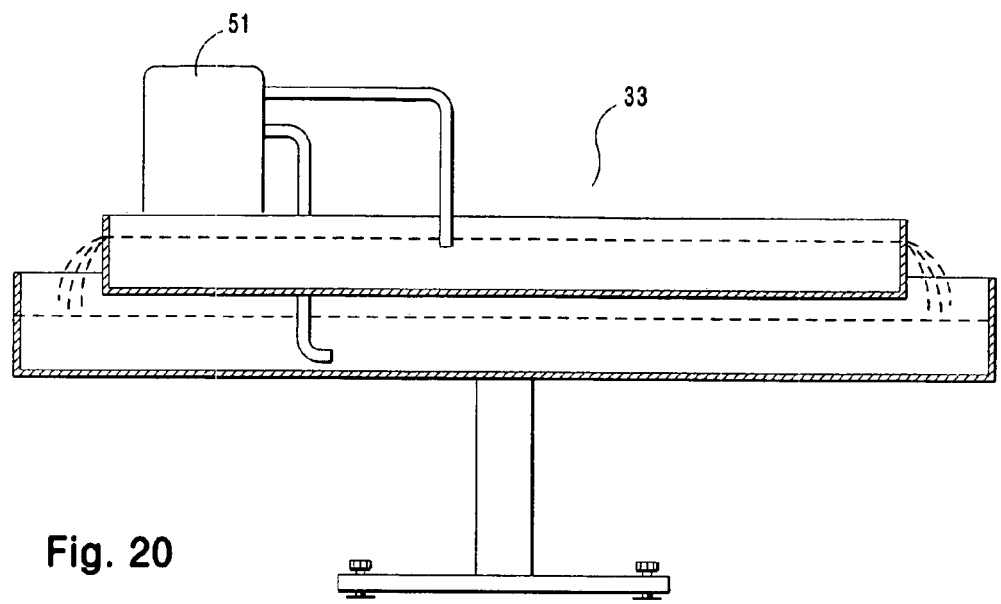
FIG. 20 is a diagrammatic view of the drawing bath shown in FIG. 20 from the side showing the water level in such bath.

FIG. 20 is respectively a diagrammatic plan view and a diagrammatic side view of the drawing bath arrangement 33 shown in FIGS. 15, 18 and 19.

As will be understood, a thin plastic stiffener tube section can be more or less continuously extruded from the small extruder 29 passed through cooling bath 30 and then a micrometer shown diagrammatically in 15 after which the extruded tubing still in a disordered amorphous state as a result of having passed immediately through the cooling bath 30 may then be passed between the two godets while being elongated between the two godets 32 and 35 in the carefully controlled heating bath 33. The tubing is thus entered into a stressed elongated condition and held in such condition by intramolecular forces. However, if such tubing is later heated to a critical condition it will revert to its previous unstressed condition and will return to its shorter but greater diameter condition. This revision is taken advantage of in the present invention by first severing the tubing while still stressed as shown in FIG. 12 into short lengths appropriate for strengthening or stiffening the proximal section of a catheter just back from the distal flexible tip sufficient to reinforce or stiffen a catheter in the portion of the catheter contained in an epidural needle as the flexible tip is pushed into the predominantly vascularized fatty tissue serving largely as a cushion between the vertebrae and the delicate spinal cord protected by the dura mater and the cerbro-spinal fluid between the arachnoid membrane and highly vascularized pia mater next to the spinal cord. The flexible tip of the catheter is too soft and flexible to pierce vascular tissue in the epidural space especially or most importantly venous tissue which leads into progressively larger vessels conducting anything injected into them quickly and possibly disastrously away from the area of injection to other parts of the body and particularly the heart which may be adversely affected by a heavy dose of anesthetics. Even though the soft flexible tip of the catheter is unable to pierce venous tissue, however, by the use of the internal stiffeners of the present invention, the portion of the catheter away from the tip still in the epidural needle is stiffened sufficiently so it is easily moved through the epidural needle even when resistance is provided by tissues mostly of fatty nature through which the flexible tip is being inserted.

As shown in FIG. 13 the individual stiffeners may be inserted into the end of the flexible tip catheter by passing then into the end of the tube of a catheter on either a manual mandrel or a mechanically operated mandrel. It may be desirable to lay the catheter tubing while this is being done in a straight V-groove upon a plate to both keep the catheter tubing straight and still. A series of V-grooves may be provided so that a series of stiffeners can be consecutively inserted into a series of catheters just back from the tip and then treated in a heat treatment atmosphere or bath immediately thereafter. The series of catheters may be immobilized in the V-grooves during such operation by a second plate clampable to or securable over the V-grooves of the first plate by any suitable clamping or support means.

Figure 21:
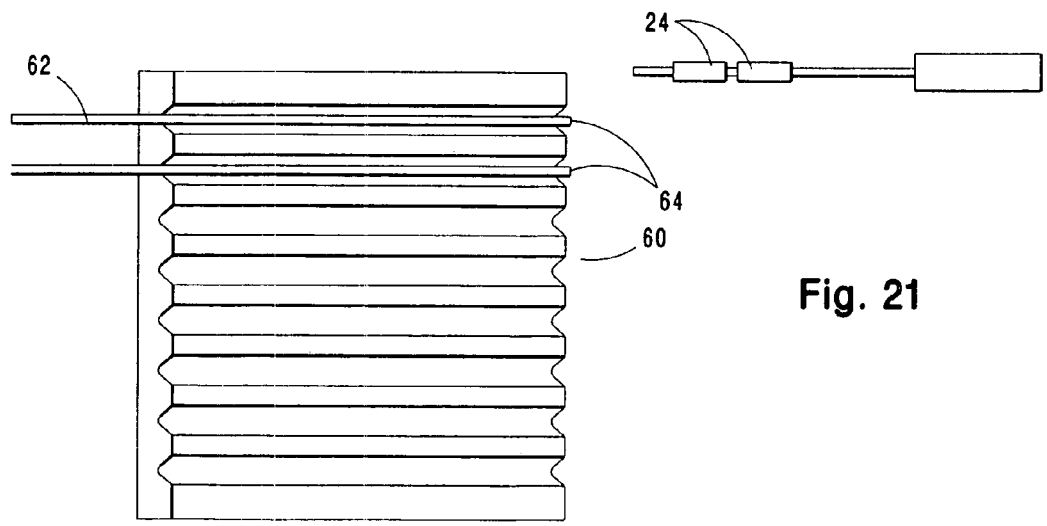
FIG. 21 is an isometric view of a grooved catheter stabilizing surface for holding one or more catheters in position for insertion of a stiffening member in accordance with the invention.

A grooved plate or base 60 with a series of catheters 62 laid in V-grooves 64 of the surface to hold and straighten such catheters is shown in FIG. 21 with a mandrel with two stiffeners 64 approaching from one side. It will be understood that the small stiffeners 64 will be inserted into the ends of the catheters and away from or beyond the ends approximately the same distance from the end that the flexible end of the catheter is expected or desired to extend from the epidural needle when inserting into the epidural space during an injection and the mandrel will be manipulated to leave the stiffener in such space and withdrawn. The other stiffener will then be inserted into an other catheter section and after the mandrel is withdrawn the mandrel will be withdrawn after which the stiffeners together with the catheters can be exposed to the proper heat to relieve the drawing stress in the stiffeners and cause them to expand laterally and interlock with the walls of the catheter tubes to stiffen that part of the catheter.

It will be readily recognized from the above description that a very practical and effective stiffened flexible tip catheter can be made in accordance with the present invention by the procedure of the invention by which not only better and more easily produced flexible tip catheters can be made, but which is eminently practical and efficient both for batch type operations and continuous operations.

While the invention has been described for a catheter having a single lumen from one end to the other, it will be recognized that in the case of a multiple lumen catheter in which the injection of several substances can be made independently the stiffener of the present invention can be made, the stiffener of the invention can be placed in one or more of such lumens. In some cases, the insertion of a stiffener in a single lumen of a multi-lumen catheter may be sufficient to stiffen the catheter for efficient passage through an epidural needle. However, in most cases the use of multiple stiffeners will be most effective.

It will also be recognized that if the lumen of a catheter should be for some reason other than cylindrical in shape, the stiffener may be made in a corresponding configuration, although when expanding due to relaxation of previous stress configuration, the stiffener may adjust itself to the configuration of the lumen present even if not initially of the same configuration.

While the present invention has been described at some length and with some particularity with respect to the several described embodiments, it is not intended that it should be limited to any such particulars or embodiments or any particular embodiments, but it is to be construed with reference to the appended claims so as to provide the broadest possible interpretation of such claims in view of the prior art and, therefore, to effectively encompass the intended scope of the invention.

I claim:

1. A method of making an epidural hollow catheter section including a flexible tip comprising:
   (a) providing a hollow tubular plastic catheter section with a helical reinforcement within such hollow section,
   (b) providing a drawn oriented tubular stiffening section having an external diametrical dimension just small enough to fit within the helical reinforcement within the hollow tubular plastic catheter section and a length appropriate to the length of epidural needle to be used with the catheter section,
   (c) inserting the tubular stiffening section into the lumen within the helically reinforced catheter to a position just beyond the length of flexible tip desired,
   (d) exposing the section of catheter containing the stressed tubular stiffening section to a stress relief treatment effective to relieve the stress in the stiffening section causing it to expand laterally to securely contact the inside of the hollow (with the helical reinforcement) helically reinforced plastic catheter,
   (e) whereby the catheter section is stiffened in the length of the catheter containing the expanded stiffener section.

2. A method of making an epidural catheter in accordance with claim 1 including a flexible tip wherein the stress relief treatment is a heat treatment.

3. A method of making and applying a stiffening material to a stylet-free epidural catheter comprising:
   (a) producing a length of draw stressed plastic tubing by elongating such tubing uniformly until its outer diameter is uniformly somewhat less than the lumen of an epidural catheter which is to be stiffened,
   (b) severing the uniformly elongated tubing into longitudinal length segments equal to the portion of the length of a plastic epidural catheter it is wished to stiffen,
   (c) inserting at least one of such segments into the lumen of a plastic catheter tube in the portion of such catheter tube it is desired to stiffen,
   (d) applying a stress relief operation to the inserted segment whereby the stress in such segment is relieved and the stress relieved segment increases in diameter sufficiently to securely engage the sides of the lumen of the catheter.

4. A method according to claim 3 wherein the stress relief treatment is a heat treatment and the plastic epidural catheter is internally stiffened by a spiral wire reinforcing means.

5. A method according to claim 4 wherein the at least one segment is inserted into the lumen of the catheter while the catheter is laid out in an appropriate securing means and during the stress relief treatment the surface of the segment becomes interengaged at its surface with the spiral helical reinforcing means within the lumen of the catheter tube.

6. A method for stiffening a flexible tip epidural catheter containing a helical reinforcement comprising:
   (e) orienting by elongation a section of tubular plastic extrusion to an outside diameter somewhat less than the inside diameter of the lumen of the catheter,
   (f) trimming the resulting elongated and oriented tubular section to a length suitable for stiffening a portion of the distal end of a flexible tip expanded catheter at a position spaced from the flexible tip,
   (g) inserting the trimmed tubular section into the distal end of the catheter lumen away from the flexible end, and
   (h) expanding the section of oriented plastic into contact with the walls of the lumen by heat treatment.

7. A method for stiffening a flexible tip epidural catheter in accordance with claim 6 wherein the epidural catheter is reinforced with a spiral reinforcing means adjacent its interior lumen and the outer surface of the stress relieved tubular stiffening section becomes interengaged at its outer surface with the spiral reinforcing means.

* * * * *